United States Patent
Werner et al.

(12) 
(10) Patent No.: US 7,083,920 B2
(45) Date of Patent: Aug. 1, 2006

(54) SURFACE ASSEMBLY FOR IMMOBILIZING DNA CAPTURE PROBES IN GENETIC ASSAYS USING ENZYMATIC REACTIONS TO GENERATE SIGNAL IN OPTICAL BIO-DISCS AND METHODS RELATING THERETO

(75) Inventors: Martina Elisabeth Werner, Aliso Viejo, CA (US); Ramon Magpantay Valencia, Aliso Viejo, CA (US); John Francis Gordon, Irvine, CA (US)

(73) Assignees: Nagaoka & Co. Ltd., Hyogo (JP); Burnstein Technologies, Inc., Irvine, CA (US)

( * ) Notice: Subject to any disclaimer, the term of this patent is extended or adjusted under 35 U.S.C. 154(b) by 716 days.

(21) Appl. No.: 10/150,702

(22) Filed: May 17, 2002

(65) Prior Publication Data

US 2003/0059803 A1 Mar. 27, 2003

Related U.S. Application Data

(60) Provisional application No. 60/292,110, filed on May 18, 2001, and provisional application No. 60/313,917, filed on Aug. 21, 2001.

(51) Int. Cl.
*C12Q 1/68* (2006.01)
*C12P 19/34* (2006.01)

(52) U.S. Cl. .................. 435/6; 435/91.2; 435/287.2; 422/68.1

(58) Field of Classification Search .............. 435/6, 435/91.2, 287.2; 422/68.1
See application file for complete search history.

(56) References Cited

U.S. PATENT DOCUMENTS

| | | | | |
|---|---|---|---|---|
| 5,683,872 | A | * | 11/1997 | Rudert et al. ............... 435/6 |
| 5,741,647 | A | | 4/1998 | Tam |
| 5,922,617 | A | | 7/1999 | Wang et al. |
| 5,935,785 | A | | 8/1999 | Reber et al. |
| 6,020,187 | A | | 2/2000 | Tam |
| 6,030,581 | A | | 2/2000 | Virtanen |
| 6,110,748 | A | * | 8/2000 | Reber et al. ............. 436/518 |
| 6,153,384 | A | | 11/2000 | Lynch et al. |
| 6,225,625 | B1 | | 5/2001 | Pirrung et al. |
| 6,228,580 | B1 | | 5/2001 | Blumenfeld et al. |
| 6,261,781 | B1 | | 7/2001 | Kolesar |
| 6,277,570 | B1 | | 8/2001 | Wood et al. |
| 6,294,326 | B1 | | 9/2001 | Carrino et al. |
| 6,342,349 | B1 | * | 1/2002 | Virtanen ..................... 435/6 |
| 6,727,103 | B1 | * | 4/2004 | Reber et al. ............. 436/518 |

* cited by examiner

*Primary Examiner*—Kenneth R. Horlick
(74) *Attorney, Agent, or Firm*—Knobbe, Martens, Olson & Bear LLP

(57) ABSTRACT

The present invention relates to methods and systems for the detection of specific sequences of nucleic acids or oligonucleotides. It relates more particularly to a conjugated enzyme based assay system utilizing reflective and/or transmissive optical bio-discs for detection of specific sequences of nucleic acids. In the assay according to the present invention, an enzyme reaction is used to detect the presence of an analyte (DNA or RNA) in a microchannel in an optical bio-disc. The analyte is immobilized by hybridization with a specific capture probe on a capture layer on the surface and the signal that is generated is localized and specific. The signal can be in the form of a pellet, a fluorescent product, and/or a colored product, and can be detected and quantified by an optical bio-disc reader utilized in conjunction with the inventions hereof. This assay is thus quantitative in nature.

20 Claims, 30 Drawing Sheets

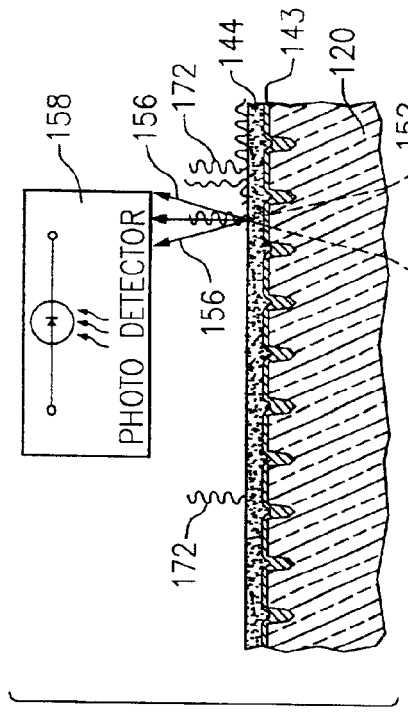
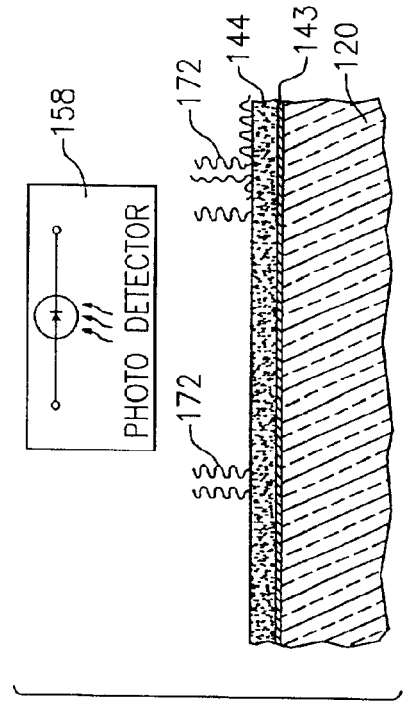
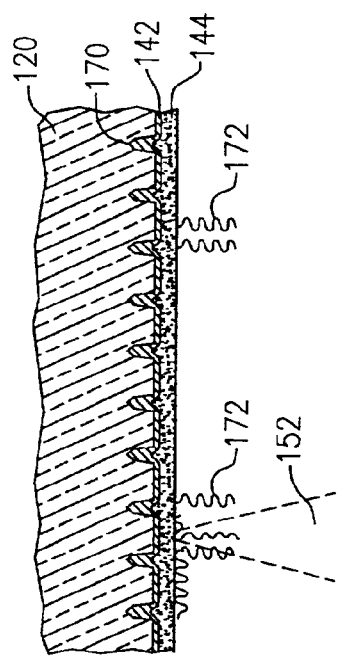
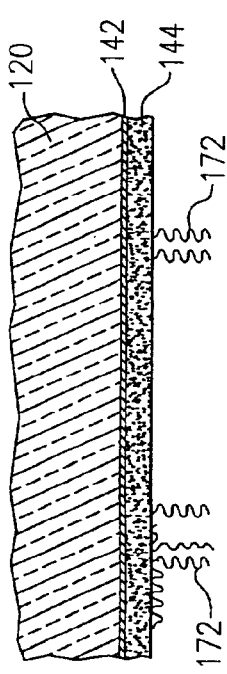
FIG. 12
FIG. 13
FIG. 14
FIG. 15

FIG. 36

SURFACE ASSEMBLY FOR IMMOBILIZING DNA CAPTURE PROBES IN GENETIC ASSAYS USING ENZYMATIC REACTIONS TO GENERATE SIGNAL IN OPTICAL BIO-DISCS AND METHODS RELATING THERETO

CROSS-REFERENCE TO RELATED APPLICATIONS

This application claims the benefit of U.S. Provisional Applications, Ser. Nos. 60/292,110, filed May 18, 2001, and 60/313,917, filed Aug. 21, 2001, the contents of which are hereby incorporated by reference in their entireties.

BACKGROUND OF THE INVENTION

The present invention relates to methods and systems for the detection of specific sequences of nucleic acids or oligonucleotides, including deoxyribonucleic acids (DNA) and ribonucleic acids (RNA). It relates more particularly to a conjugated enzyme based assay system utilizing reflective and/or transmissive optical discs for detection of specific sequences of nucleic acids.

Assay systems utilizing optical discs have been described. See, for example, Virtanen, U.S. Pat. No. 6,030,581 entitled "Laboratory in a Disk". Such systems have enormous potential in the field of medicine, for diagnostic and other clinical assays, as well as in fields such as environmental testing and the like. Nonetheless, there remains a continuing need to develop assays that are faster, more efficient, and more economical.

Commonly assigned U.S. application Ser. No. 10/035,836 discloses a bead based DNA assay developed for the optical disc platform. Although such assays are qualitatively reproducible, quantitation of bead binding through different methods showed relatively high variations.

Enzyme assays have been widely used in a microtiter plate format. Commonly assigned U.S. Provisional Application Ser. No. 60/353,017, entitled "Data Capture and Signal Processing for Colorimetric and Fluorescent Assays as Implemented on Reflective Optical Analysis Discs", filed on Jan. 29, 2002, discloses an enzyme assay implemented in an optical bio-disc system. In this assay, the reactants are not immobilized on the disc surface, and the reporter is not localized. This format is very useful for the detection of small molecules, but is not easily adapted to macromolecules, such as antibodies and DNA.

Assays that detect the presence of specific sequences of nucleic acids have a number of applications. For example, nucleic acid detection systems are used to test for the presence of specific disease causing agents, such as viruses or bacteria, in biological samples taken from patients. Nucleic acid detection systems are also used to test water and soil samples for specific microorganisms. Indeed, nucleic acid testing can be used to identify particular strains or types of a microorganism, which may have important implications for the appropriate response or treatment. Nucleic acid testing is also helpful in monitoring agricultural products as, for example, in testing for the presence of genetically modified crop products. As is well known, nucleic acid testing has important forensic applications as well.

What is needed, therefore, is a rapid, efficient, and economical assay system for testing various samples for specific nucleic acid sequences that also provides reproducible quantitation of the target nucleic acid.

SUMMARY OF THE INVENTION

This invention relates to identification of at least one target DNA or RNA that may exist in a sample and test methods relating thereto. The invention is further directed to an optical bio-disc used to test a sample of DNA or RNA for a target DNA or RNA of a prescribed sequence. The bio-disc includes a flow channel having target or capture zones, a return channel in fluid communication therewith, and in some embodiments a mixing chamber in fluid communication with the flow channel. The bio-disc may be implemented on an optical disc including an information encoding format such as CD, CD-R, DVD, DVD-R, any standard optical disc format, or a modified version thereof. Methods of manufacturing the optical bio-disc according to the present invention are also provided.

A bio-disc drive assembly is employed to rotate the disc, read and process any encoded information stored on the disc, and analyze the DNA samples in the flow channel of the bio-disc. The bio-disc drive is thus provided with a motor for rotating the bio-disc, a controller for controlling the rate of rotation of the disc, a processor for processing return signals form the disc, and an analyzer for analyzing the processed signals. The rotation rate is variable and may be closely controlled both as to speed, direction, and time of rotation.

The bio-disc drive assembly may also be utilized to write information to the bio-disc either before, during, or after the test material in the flow channel and target zones is interrogated by a read beam of the drive and analyzed by the analyzer. The bio-disc may include encoded information for controlling the rotation rate of the disc, providing data acquisition and processing information specific to the type of DNA or RNA test to be conducted, for displaying the results on a monitor associated with the bio-drive, and/or saving the results on a hard drive, floppy disc, on the bio-disc itself, or on any other recordable media. A reflective disc format suitable for use in the present invention is disclosed in commonly assigned U.S. Provisional Application No. 60/249,391 entitled "Optical Disc Assembly for Performing Microscopy and Spectroscopy Using Optical Disc Drive," hereby incorporated by reference in its entirety.

In an alternative embodiment, a transmissive disc format may be used in which the interrogation beam is transmitted through the target zone and detected by a top detector. Such a transmissive disc format is disclosed in commonly assigned U.S. Pat. No. 6,327,013 and in commonly assigned U.S. Provisional Applications Nos. 60/293,917; 60/303,437; and 60/323,405, entitled "Optical Discs and Assemblies for Detection of Microscopic Structures Using Focal Zone Control," hereby incorporated by reference in their entireties.

Development of a DNA based assay for CD, CD-R, DVD, DVD-R, or any standard optical disc format and variations thereof according to the present invention, includes attachment of conjugated enzymes to the disc surface as a detection method. These enzymes are selected so as to yield, in the presence of a suitable substrate, reaction products that an interrogation beam of the drive can "see" or detect by a change in surface reflectivity or transmittance caused by the reaction products.

The enzymes are bound to the disc surface through binding agents including, for example, Streptavidin and biotin. A capture probe is attached to the disc in a capture zone, while a biotinylated target is allowed to hybridize with the capture probe. Once the target is hybridized with its respective capture probe, a Streptavidin conjugated enzyme introduced into the capture zone and allowed to bind to the biotin on the target. In this manner, the enzyme is attached to a disc surface. In a subsequent centrifugation (or wash) step, all unbound enzyme is removed. Substrate appropriate for the bound enzyme is added, and the enzymatic reaction is allowed to take place. The enzyme reaction products deposit on the disc surface at or near the bound enzyme, where they can be detected and quantitatively measured to provide both a qualitative and quantitative measurement of the analyte of interest.

In an alternative embodiment of the present invention, the enzymes are bound to the disc surface through DNA hybridization. A capture probe is attached to the disc, while the Streptavidin conjugated enzyme is attached to a biotinylated signal probe. Each of these probes is complementary to a different portion of the target sequence, but are not complementary to each other. In the presence of a target sequence, both capture and signal probes hybridize with the target. In this manner, the enzyme is attached to a disc surface within the capture zone. In a subsequent centrifugation (or wash) step, all unbound enzyme is removed. Substrate appropriate for the bound enzyme is added, and the enzymatic reaction is allowed to take place. The enzyme reaction products deposit on the disc surface at or near the bound enzyme, where they can be detected and quantitatively measured by a beam of electromagnetic radiation to provide both a qualitative and quantitative measurement of the analyte of interest.

The DNA capture probe can be bound to an active layer, bio-layer, or binding layer by passive adhesion or adsorption, electrostatic interaction (using a positively charged active layer), or covalent binding, achieved by using an activated active layer and a modified DNA wherein the modified DNA can covalently bind onto the active layer. For example, an aminated DNA can covalently bind onto a polystyrene co-maleic-anhydride active layer. This active layer may be formed from a variety of media including nitrocellulose, polystyrene, polycarbonate, gold, activated glass, modified glass, or modified media. The modified media includes anhydride groups, activated carboxylate groups, or carboxylic acid aldehyde groups.

After DNA hybridization, a neutravidin- or streptavidin-conjugated enzyme as, for example, alkaline phosphatase or horseradish peroxidase, is bound to the biotinylated DNA as described above. Then a solution of enzyme substrate is added and reacts with the enzyme to form a reaction product in the form of insoluble pellets or precipitate, fluorescent, and/or colored product. The pellets stay localized on the reaction spots where the DNA probe was applied, even after centrifugation of the disc.

The specific enzymatic reaction products can be detected using different methods. These methods include microscopic analysis, measurement of fluorescence signal on the disc surface using a FluorImager (Molecular Dynamics), or detection of insoluble reaction product using an optical disc reader. For example, an event counting software useful for reaction product detection in a optical disc reader is disclosed in commonly assigned U.S. Provisional Application No. 60/291,233 entitled "Variable Sampling Control for Rendering Pixelization of Analysis Results in Optical Bio-disc Assembly and Apparatus Relating Thereto," hereby incorporated by reference in its entirety. As discussed below in conjunction with FIG. 37 and in Example 5, the signal from an enzymatic reaction product, in one embodiment of the present invention, is concentration dependent using the event counting software to quantitate the data, thus making this a quantitative detection method. Moreover, a fluorescent enzymatic product may be detected by a fluorescent type disc reader while a colored product (chromagen) can be detected using a transmissive or reflective disc set-up described below. Alternatively, the signal detection and quantitation may be carried out using other methods of quantitation in conjunction the optical bio-disc reader with appropriate software. For example, the transmissive optical disc format may be used to quantify changes in light transmission or scattering as a result of generation of an enzymatic reaction product or reporter.

The DNA assay according to the present invention may be implemented in an open disc format as well as in a micro channel. In the open disc format, the reagents are spotted directly on the disc surface. Unbound reagents are removed by washing the disc. In the micro channel format, the capture probe binding is initially performed on an open disc substrate. After attaching the DNA capture probes, the channel is assembled by affixing adhesive and a cover disc or cap. Subsequent steps are performed in the closed channel which is filled with liquids such as buffer solutions, enzyme solutions, and DNA test samples which are analyzed for the presence of a target sequence.

Brief Overview of the Assay

In the assay according to the present invention, an enzyme reaction is used to detect the presence of an analyte (DNA or RNA) in a microchannel on an optical bio-disc. The analyte is immobilized on a capture layer on the surface, and the signal that is generated is localized and specific, as, for example, by the formation of an insoluble product of the enzyme reaction. The signal can be in the form of a pellet, a fluorescent product, and/or a colored product, and can be detected and quantified by an optical bio-disc reader utilized in conjunction with the inventions hereof. This assay is thus quantitative in nature. In addition, the formation of the pellet in one embodiment hereof is facilitated by a layer of nitrocellulose on the disc surface, which supports binding of the capture layer and formation and retention of the pellet.

Analytes

The present invention is directed to the detection and analysis of target nucleic acid sequences present in test samples. Target nucleic acids suitable for use with the present invention include both deoxyribonucleic acid (DNA) and ribonucleic acid (RNA), including mRNA, rRNA, hnRNA and tRNA.

Target nucleic acid may be used directly from a biological sample, but preferably is amplified prior to testing via polymerase chain reaction (PCR) or isothermal amplification to generate amplicons. If using PCR for amplification, RNA may first be reverse transcribed into DNA using techniques well known in the art. Target nucleic acid may be single stranded or double stranded. If double stranded, the nucleic acid may be denatured prior to hybridization with capture DNA.

In one embodiment of the present invention, primers labeled with biotin are used in PCR reactions to yield biotin-labeled target DNA amplicons, which are then tested in the bio-disc assay as described below. Amplicons of various lengths are suitable for use in the present invention, with a preferred length from about 20 bases (or base pairs) to about 4000 bases (or base pairs), more preferably from about 200 to about 400 bases or base pairs.

The present invention may be used to detect specific nucleic acid sequences in a wide variety of biological samples, including but not limited to bodily fluids such as whole blood, serum, plasma, saliva, urine, lymph, spinal fluid, tears, mucous, semen and the like, agricultural products, food items, waste products, environmental samples, such as soil and water samples, or any other sample containing, or suspected of containing specific nucleic acid sequences of interest. For example, the present invention may be used to detect the presence of particular strains of microorganisms, such as viruses or bacteria, in body fluids or environmental samples, by detecting the presence of particular nucleic acid sequences in the sample. In another example, the present invention may be used to detect the presence of genetically modified agricultural products in food items. In yet another example, the present invention may be used to identify specific pulmonary infectious agents using a microarray format. Other uses of the present invention will be apparent to those of skill in the art.

Capture DNA

Capture DNA oligonucleotides, or probes, are immobilized onto a bio-disc and are hybridized to target DNA or RNA to thereby "capture" the target nucleic acid in the target zone for detection. Capture DNA may be single stranded or partially double stranded near the attachment point to the active layer on the bio-disc. One preferred embodiment of the capture DNA includes a partially double stranded DNA. The double strand us located at the reactive end of the probe, such as the amino end, because the double strand has been found to more effectively project the capture probe erectly or upwardly from the active layer as compared to ssDNA in some instances. An extension or spacer including, for example, ssDNA and PEG, may be employed so as to increase the hybridization efficiency of the capture probe with the target. The sequence of the capture DNA is selected so as to hybridize directly with target DNA or RNA, thereby forming a complex comprising capture DNA, target DNA or RNA and conjugated enzyme bound thereto as depicted below in FIGS. 33A–33G and 35A–35F.

In an alternative embodiment described below, signal DNA is also be present in this complex. In this embodiment, the signal DNA sequence is complementary to a portion of the target DNA or RNA, but is not complementary to the capture DNA. As one portion of the target DNA hybridizes with capture DNA, while a different portion hybridizes with signal DNA, a complex forms in which the target DNA acts as a "bridge" between the capture DNA and signal DNA as described below in conjunction with FIGS. 34A–34H.

Signal DNA

In one embodiment of the present invention, target DNA hybridizes directly with capture DNA bound to the active layer of a bio-disc. In an alternative embodiment, target DNA is used as a "bridge" between signal DNA and the capture DNA. In the alternative embodiment, the sequence of the signal DNA is selected so as to contain a region that is complementary to the target DNA, but which contains no sequence complementarity with the capture DNA, such that the signal DNA will not form a complex with the capture DNA in the absence of target DNA. The target DNA contains a first region of complementary sequence to the capture DNA, permitting hybridization of the first region of the target DNA to the capture DNA, and a second region of complementary sequence to the signal DNA, permitting hybridization of the signal DNA to the second region of the target DNA, thereby linking or bridging the signal DNA to the capture DNA.

The target DNA may be of any length suitable to effectively immobilize itself and the signal DNA to the capture DNA. Typically, signal DNA and capture DNA are from about 10 bases to about 100 bases in length, preferably from about 20 bases to about 60 bases in length. Typically, the target DNA amplicons have an overlap of from about 20 bases to about 40 bases with the signal DNA and an overlap of from about 20 bases to about 40 bases with the capture DNA. Preferably, the target DNA amplicon has a GC (guanine and cytosine) content greater than 50%, within the areas of overlap between the capture probe, target, and signal probe. Although one skilled in the art will appreciate that GC content and length of the target DNA amplicon may be modulated to effectuate stable hybridization to the signal and capture DNA.

In one embodiment of the present invention, signal DNA or the target DNA is labeled with an affinity agent, such as biotin, to permit binding to conjugated enzymes via biotin/streptavidin interactions with streptavidin-conjugated enzymes.

Capture Layer Preparation

Capture DNA probes are bound to the surface of the disc through non-covalent adsorption to a layer of nitrocellulose, which is spin-coated on the disc. The layer of nitrocellulose can be applied to different types and surfaces of discs. After attaching the capture probes, microchannels may be assembled and prepared for sample application as shown and described below in conjunction with FIGS. 2A–2C, and 3A–3D.

Blocking Non-specific DNA, RNA and Protein Adsorption

After the disc is assembled, the channels are blocked with a DNA/protein blocking solution to prevent non-specific binding of target nucleic acid, signal probes and/or enzymes on the target zone. The blocking solution may be a buffer containing, for example, bovine serum albumin (BSA), salmon sperm DNA, and/or Denhardt's solution.

Sample Application

When a sample is injected into the microchannel, any target RNA or DNA present in the sample binds to the capture probe through hybridization. In one embodiment, target DNA is generated in an amplification reaction using biotinylated primers, resulting in biotinylation of the target DNA. Following hybridization, unbound amplicon DNA is removed with a wash step.

In another embodiment of the assay, the target RNA or DNA is not directly biotinylated. Rather, a biotinylated signal DNA probe is used. In this embodiment, target DNA is amplified by PCR or isothermal amplification using non-biotinylated primers (target RNA is similarly generated by isothermal amplification). The target DNA is then hybridized to a biotinylated signal DNA probe.

Signal Generation

In one embodiment, a solution of streptavidin- or neutravidin-conjugated enzyme, such as horseradish peroxidase, is injected into the microchannel, where the enzyme binds to the biotinylated amplicon or signal probe via the streptavidin- or neutravidin-biotin interactions. Excess enzyme is removed through a wash step and the microchannel is filled with a solution of an enzyme substrate, such as TMB (3,3,5,5 tetramethylbenzidine in stable peroxide buffer), that is converted to an insoluble product, becomes luminescent or fluorescent, changes color through the enzyme reaction, or otherwise generates a detectable signal. In one embodiment, the enzyme reaction product is an insoluble precipitate that adheres to the active layer, forming a detectable precipitate as described below in conjunction with FIGS. 21 and 22A–22D.

In another embodiment, the conjugated enzyme is first dried onto a pad or membrane, which is deposited into a side chamber in fluid communication with the microchannel as illustrated in FIG. 4, below. A buffer solution is introduced into the side chamber via an input port, causing the enzyme to be released and travel into the microchannel where it can interact with the biotinylated DNA. Substrate is then introduced as above. Materials useful for the pad or membrane include filter paper, cellulose acetate, nitrocellulose, glass fiber, hydrophilic polyether sulfone, nylon, cellulose and the like.

Enzymes and Substrates

Enzymes useful in the practice of the present invention include any enzyme that may be adapted to interact with a specific nucleic acid probe, as, for example, through the interaction of an enzyme conjugated with streptavidin- or neutravidin- and with a biotin labeled DNA. The enzyme produces a detectable signal in the presence of a suitable substrate. For example, conjugated horseradish peroxidase (HRP; Pierce, Rockford, Ill.) may be used with the substrate 3,3,5,5-tetramethylbenzidine (TMB; Calbiochem cat. no. 613548, CAS-54827-17-7) in the presence of hydrogen peroxide to produce an insoluble precipitate. Horseradish peroxidase can also be used in conjunction with CN/DAB (4-chloronaphthol/3,3'-diaminobenzidine, tetrahydrochloride), 4-CN (4-chloro-1-napthol), AEC (3-amino-9-ethyl carbazol) and DAB (3,3-diaminobenzidine tetrahydrochloride) to form insoluble precipitates. Similarly, the enzyme alkaline phosphatase (AP) can be used with the substrate bromochloroindolylphosphate in the practice of the present invention. Other suitable enzyme/substrate combinations will be apparent to those of skill in the art.

Detection

The signal from the enzyme reaction can be read with an optical bio-disc reader. Either a bottom detector on a disc with a reflective cover, or a top detector with a transmissive disc can be employed with the optical bio-disc reader for the assay and disc inventions disclosed herein and described in detail below in connection with FIGS. 1, 2A–2C, 3A–3D, 5, and 6–14.

Disc Implementation

The assays and methods of the present invention may be advantageously implemented on an analysis disc, modified optical disc, or bio-disc. The bio-disc may include a flow channel having target or capture zone, a return channel in fluid communication therewith, and in some embodiments a mixing chamber and/or a side chamber in fluid communication with the flow channel.

The bio-disc may be implemented on an optical disc including an standard information encoding format such as CD, CD-R, DVD, DVD-R or a modified version thereof. The bio-disc may include encoded information for performing, controlling, and post-processing the test or assay. For example, such encoded information may be directed to controlling the rotation rate of the disc. Depending on the test, assay, or investigational protocol, the rotation rate may be variable with intervening or consecutive sessions of acceleration, constant speed, and deceleration. These sessions may be closely controlled both as to speed and time of rotation to provide, for example, mixing, agitation, or separation of fluids and suspensions with agents, reagents, DNA, RNA or antibodies.

Drive Implementation

A bio-disc drive assembly or reader may be employed to rotate the disc, read and process any encoded information stored on the disc, and analyze the samples in the flow channel of the bio-disc. The bio-disc drive is thus provided with a motor for rotating the bio-disc, a controller for controlling the rate of rotation of the disc, a processor for processing return signals form the disc, and an analyzer for analyzing the processed signals. The drive or disc may include software specifically developed for performing the assays disclosed herein.

The rotation rate of the motor is controlled to achieve the desired rotation of the disc. The bio-disc drive assembly may also be utilized to write information to the bio-disc either before, during, or after the test material in the flow channel and target zone is interrogated by the read beam of the drive and analyzed by the analyzer. The bio-disc may include encoded information for controlling the rotation rate of the disc, providing data acquisition, and processing, reporting and recording information specific to the type of genetic test to be conducted, and for displaying the results on a display monitor associated with the bio-drive in accordance with the assay methods relating hereto.

BRIEF DESCRIPTION OF THE DRAWINGS

FIG. 12 illustrates an embodiment of the optical bio-disc that utilizes a reflective open-face or open-disc format;

FIG. 13 illustrates an embodiment of the optical bio-disc that utilizes a transmissive open-face or open-disc format;

FIG. 14 is an alternate sectional view of the disc illustrated in FIG. 12 taken longitudinally along one of the tracks or grooves;

FIG. 15 is an alternate sectional view of the disc illustrated in FIG. 13 taken longitudinally along one of the tracks or grooves;

FIG. 36 is an example of data output collected using an optical disc reader and its respective software;

DETAILED DESCRIPTION OF THE PREFFERED EMBODIMENTS

Figure 1:
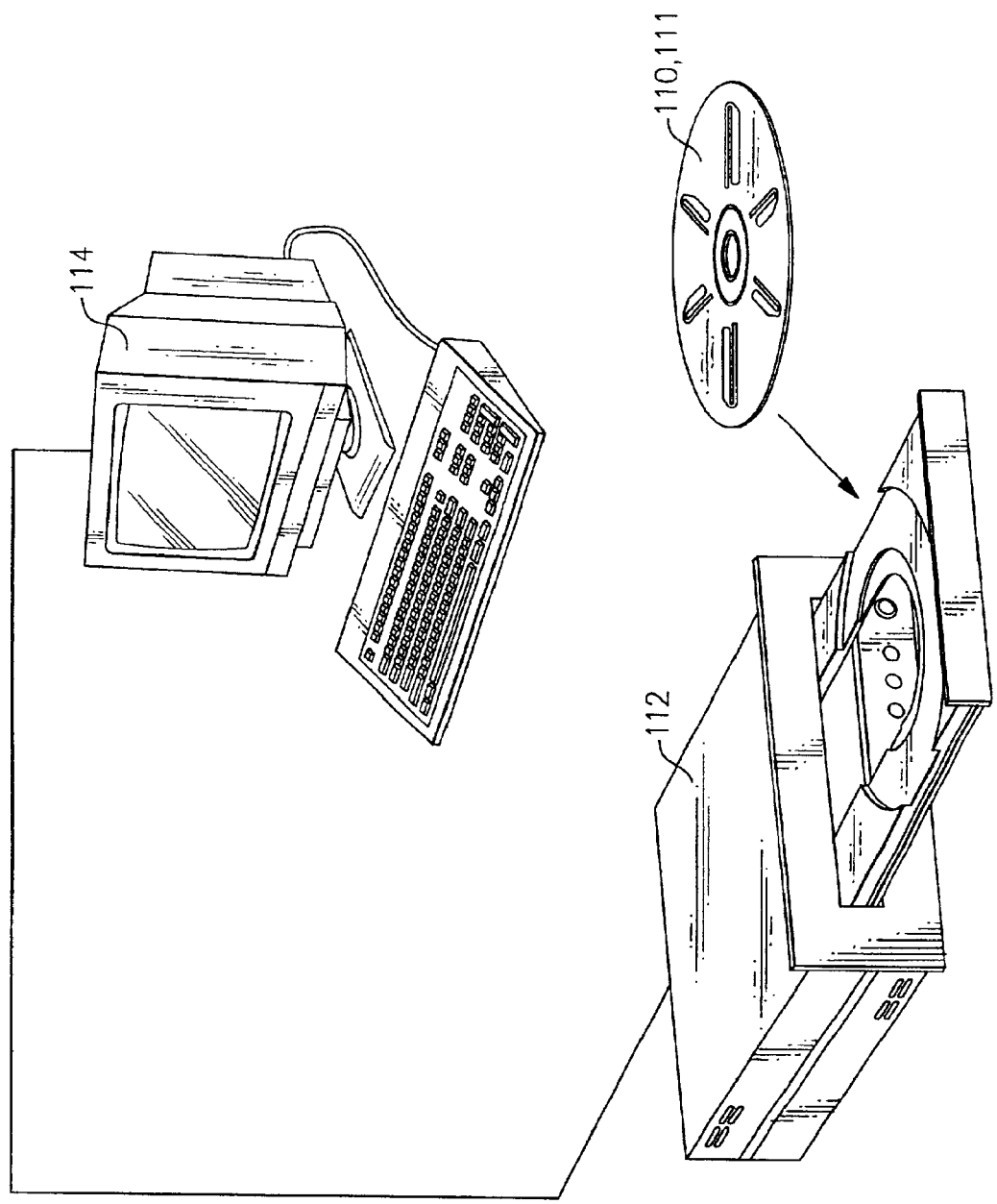
FIG. 1 is a pictorial representation of a bio-disc system according to the present invention.

Further objects of the present invention together with additional features contributing thereto and advantages accruing therefrom will be apparent from the following description of preferred embodiments of the present invention which are shown in the accompanying drawing figures with like reference numerals indicating like components throughout.

FIG. 1 is a perspective view of an optical bio-disc 110 or 111 according to the present invention. The present optical bio-disc 110 or 111 is shown in conjunction with an optical disc drive 112 and a display monitor 114.

Reflective Disc

Figure 2A:
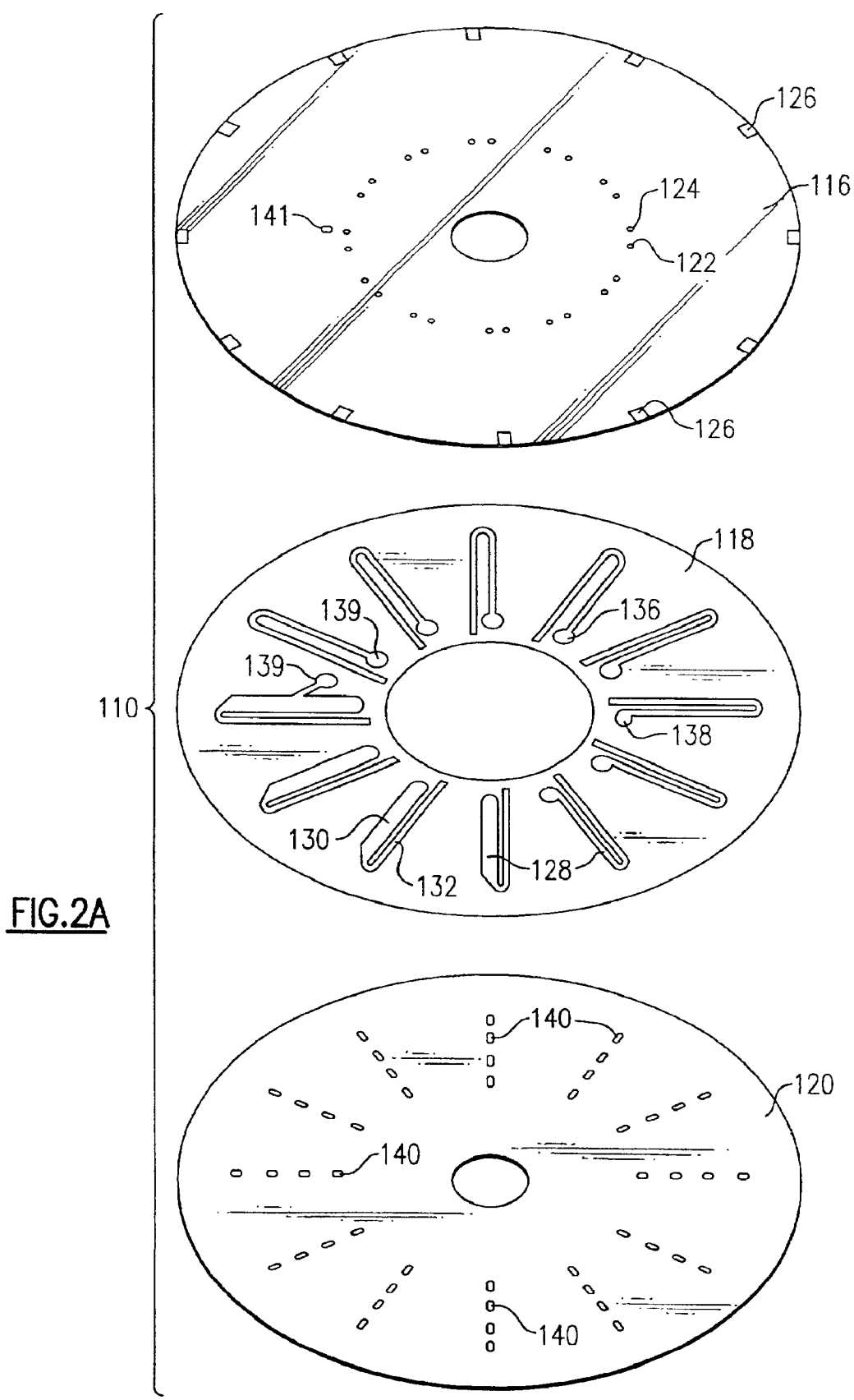
FIG. 2A is an exploded perspective view of a reflective bio-disc.

FIG. 2A is an exploded perspective view of the principle structural elements of a reflective optical bio-disc 110 or a reflective zone optical bio-disc (hereinafter "reflective disc") that may be used in the present invention. The principle structural elements include a cap portion 116, an adhesive member 118, and a substrate 120.

The cap portion 116 includes an inlet port 122, a vent port 124, and, optionally, an enzyme buffer port 141. The cap portion 116 may be formed from polycarbonate and is preferably coated with a thin reflective surface 146 on the bottom thereof as viewed from the perspective of FIG. 2A. The reflective surface 146 is best illustrated in FIG. 2C.

Figure 5:
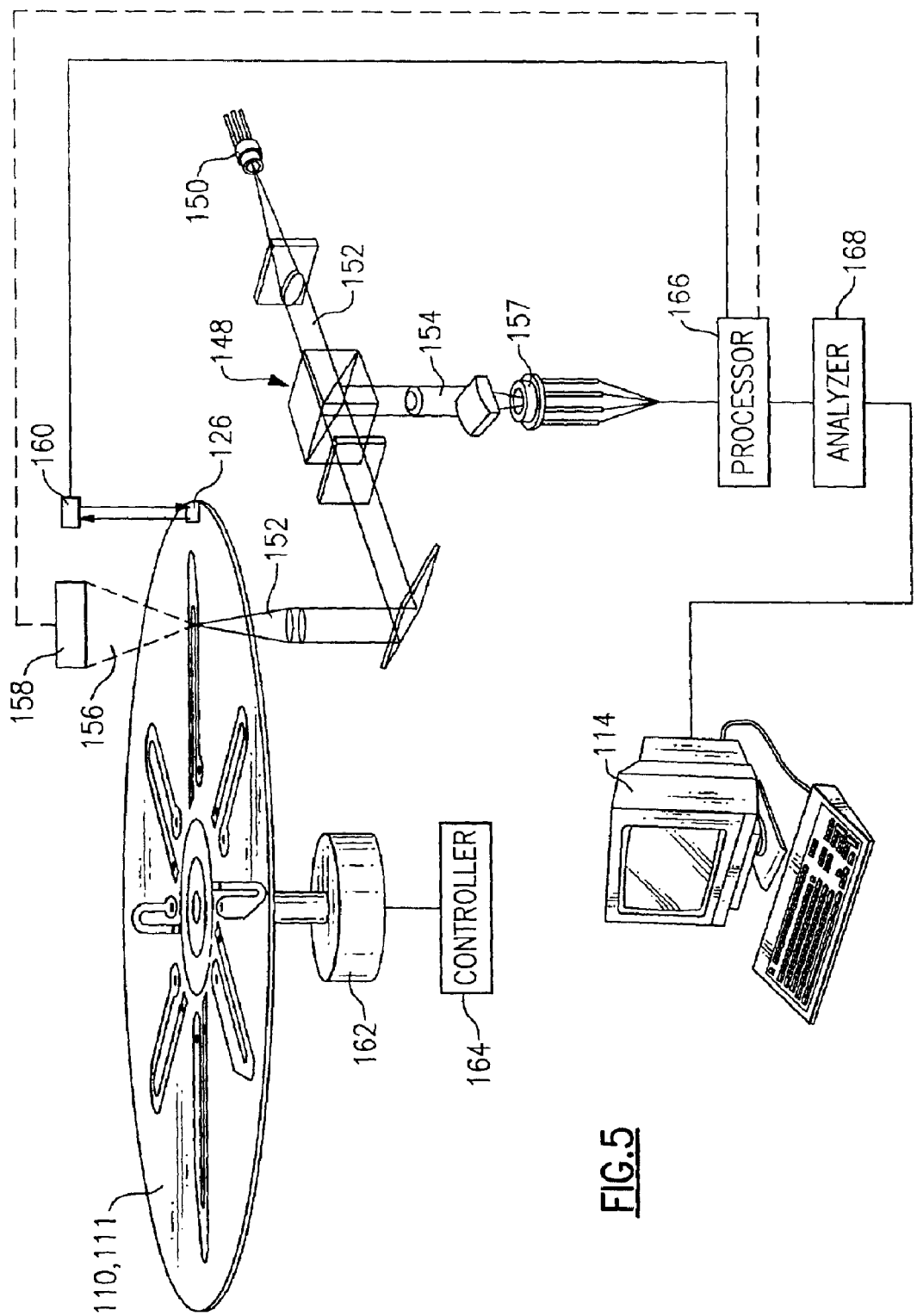
FIG. 5 is a perspective and block diagram representation illustrating the system of FIG. 1 in more detail.

In a preferred embodiment, trigger markings 126 are included on the reflective surface. Trigger markings 126 may include a clear window in all three layers of the bio-disc, an opaque area, or a reflective or semi-reflective area encoded with information that sends data to a processor 166, as shown in FIG. 5, that in turn interacts with the operative functions of the interrogation or incident beam 152, shown in FIGS. 3B and 5.

The second element shown in FIG. 2A is an adhesive member 118 having fluidic circuits or U-channels 128 formed therein. The fluidic circuits 128 are formed by stamping or cutting the member to remove plastic film and form the shapes as indicated. Each of the fluidic circuits 128 includes a flow channel 130 and a return channel 132.

Some of the fluidic circuits 128 illustrated in FIG. 2A include a mixing chamber 134. Two different types of mixing chambers 134 are illustrated. The first is a symmetric mixing chamber 136 which is symmetrically formed relative to the flow channel 130. The second is an off-set mixing chamber 138. The off-set mixing chamber 138 is formed to one side of the flow channel 130 as indicated. In one embodiment, some of the fluidic circuits 128 include a side chamber 139 in fluid communication with the flow channel 130.

The third element illustrated in FIG. 2A is a substrate 120 including target or capture zone 140. The substrate 120 is preferably made of polycarbonate and has a reflective layer 142 deposited on the top thereof, best illustrated in FIG. 2C. The target zones 140 are formed by removing the reflective layer 142 in the indicated shape or, alternatively, in any desired shape. Alternatively, the target zone 140 may be formed by a masking technique that includes masking the target zone 140 area before applying the reflective layer 142. The reflective layer 142 may be formed from a metal such as aluminum or gold.

Figure 2B:
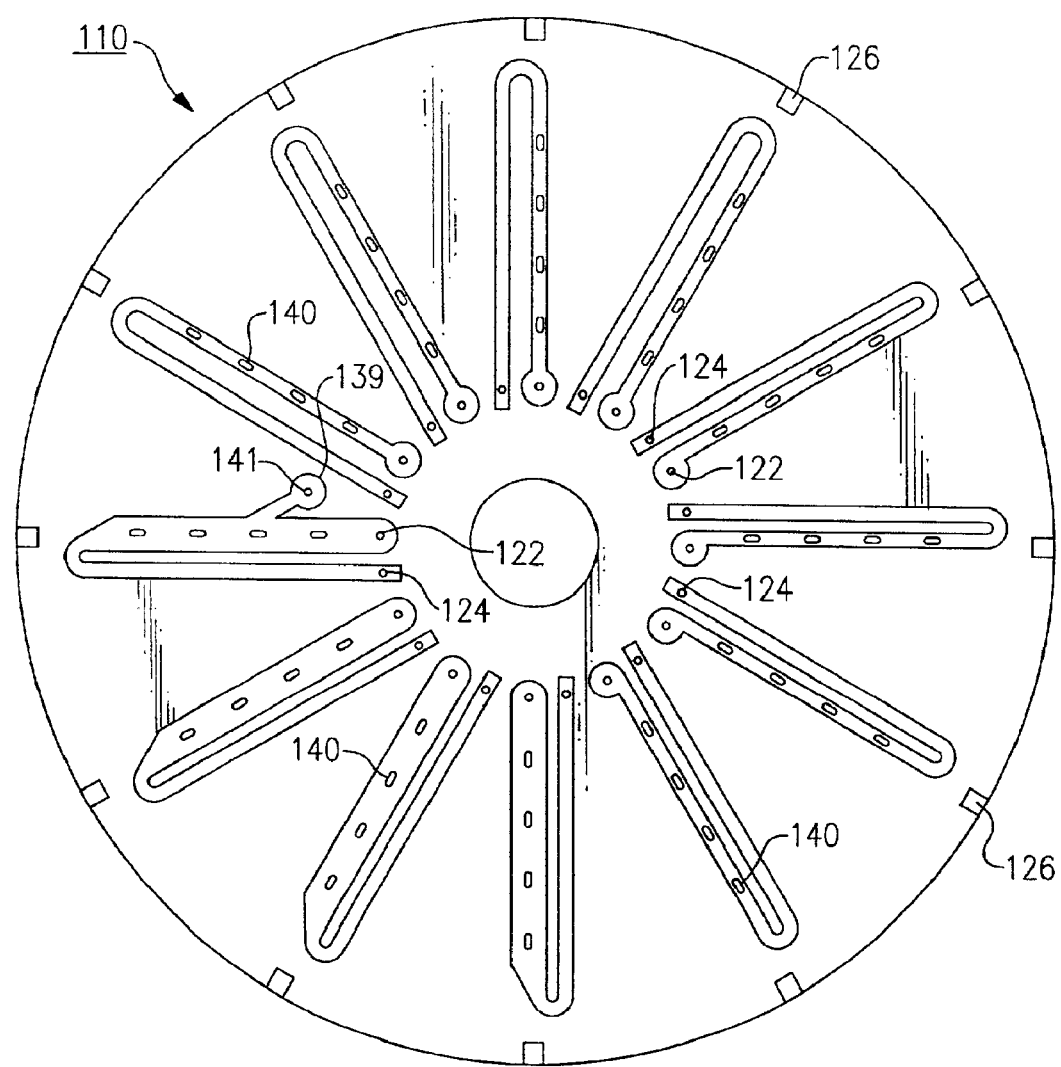
FIG. 2B is a top plan view of the optical bio-disc 110 illustrated in FIG. 2A, with the reflective layer 142 on the cap portion 116 shown as transparent.
Figure 2C:
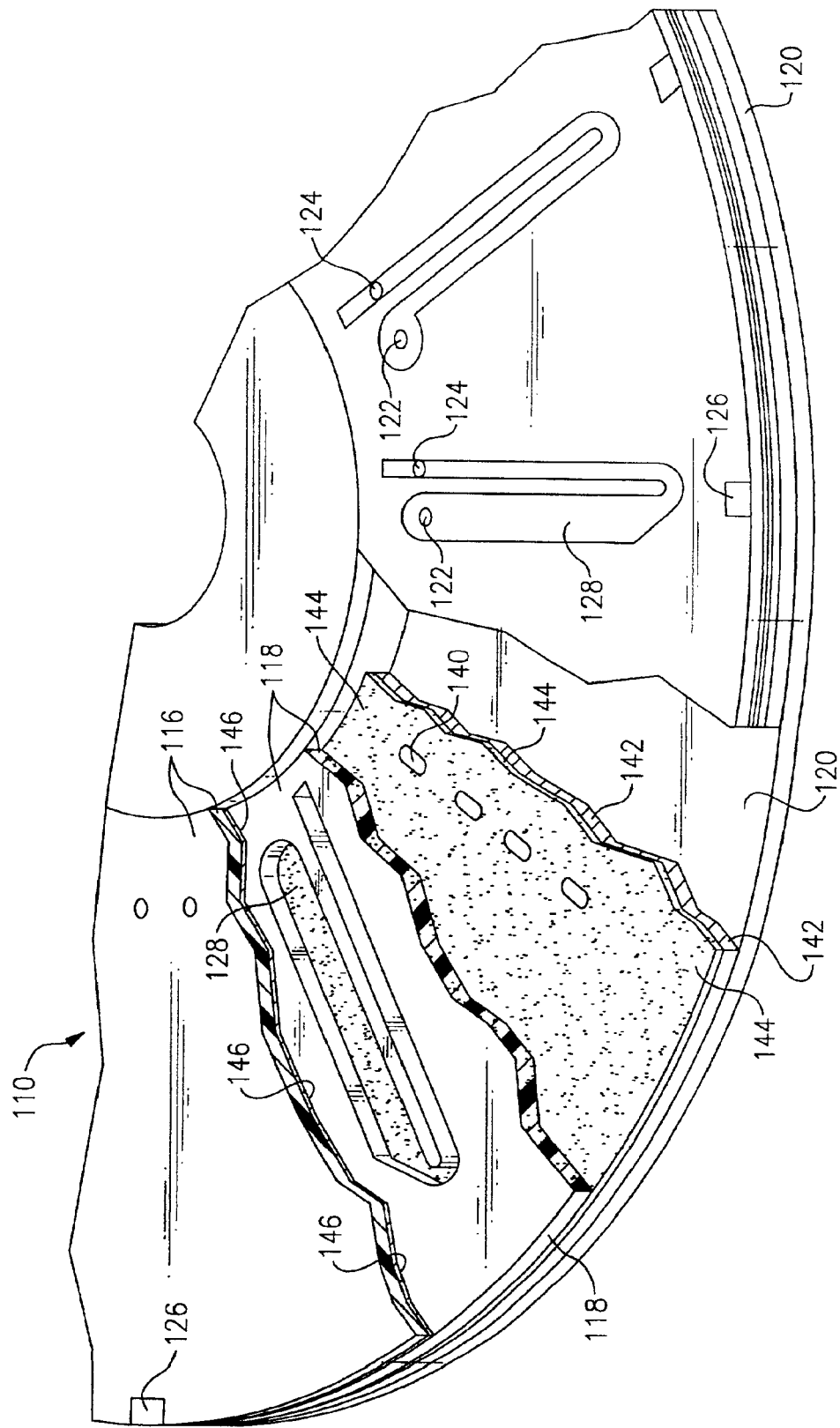
FIG. 2C is an enlarged perspective view of the optical bio-disc 110 according to one embodiment of the present invention having a portion of the various layers thereof, cut away to illustrate a partial sectional view of each principle, layer, substrate, coating, or membrane.

FIG. 2B is a top plan view of the reflective optical bio-disc 110 illustrated in FIG. 2A with the reflective surface 146 on the cap portion 116 shown as transparent to reveal the fluidic circuits 128, the target zones 140, and trigger markings 126 situated within the disc.

Referring now to FIG. 2C, there is shown an enlarged perspective view of the reflective optical bio-disc 110 according to one embodiment of the present invention, having a portion of the various layers thereof, cut away to illustrate a partial sectional view of each principle, layer, substrate, coating, and membrane. FIG. 2C shows the substrate 120 that is coated with the reflective layer 142. An active layer 144 is applied over the reflective layer 142. In the preferred embodiment, the active layer 144 is formed from nitrocellulose. Alternatively, polystyrene, polycarbonate, gold, activated glass, modified glass, or a modified polystyrene, for example, polystyrene-co-maleic anhydride, may be used. As illustrated in this embodiment, the plastic adhesive member 118 is applied over the active layer 144. The exposed section of the plastic adhesive member 118 illustrates the cut out or stamped U-shaped form that creates the fluidic circuits 128. The final principle structural layer in this embodiment of the present bio-disc is the cap portion 116. The cap portion 116 includes the reflective surface 146 on the bottom thereof. The reflective surface 146 may be made from a metal such as aluminum or gold.

Transmissive Disc

Figure 3A:
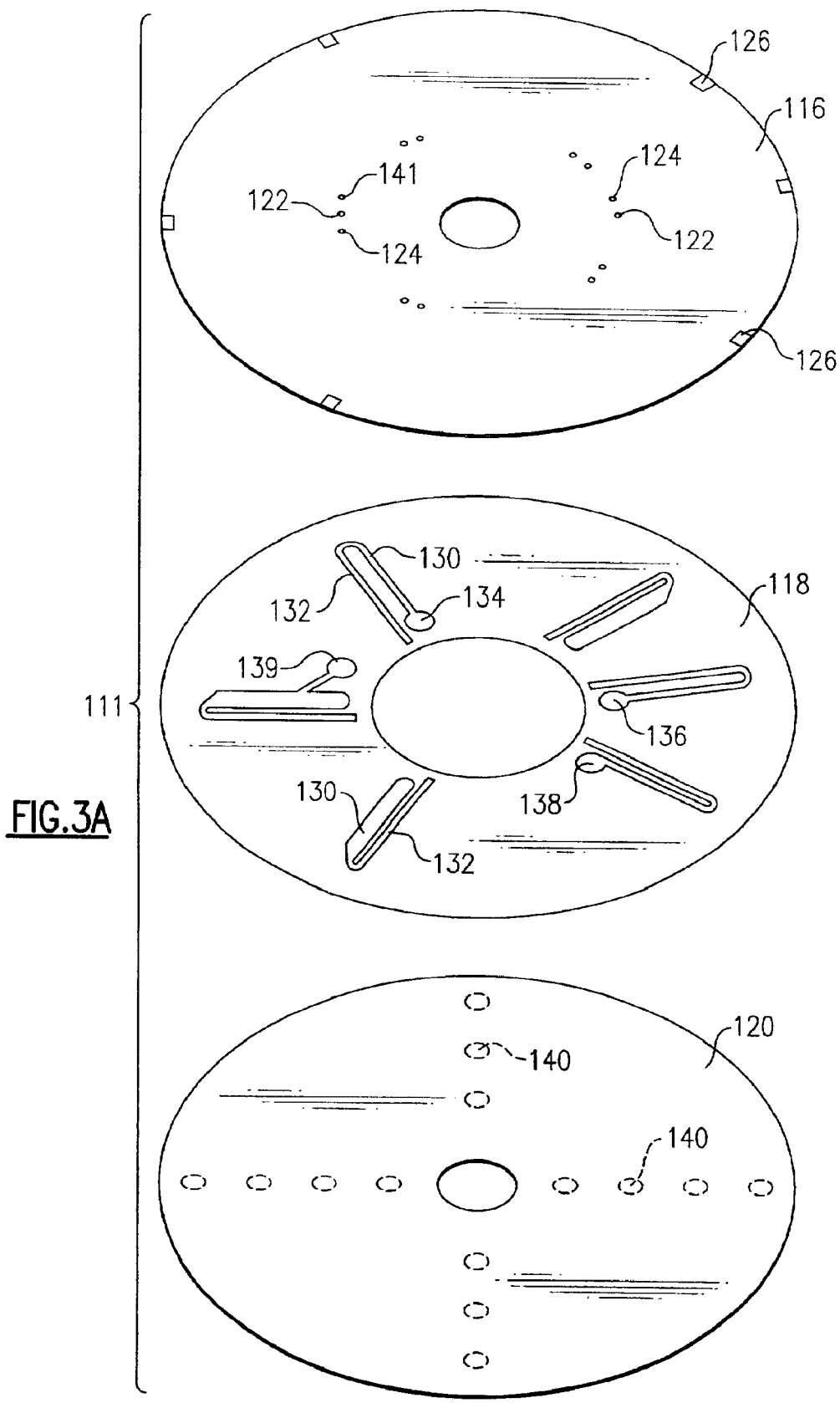
FIG. 3A is an exploded perspective view of the principle structural elements of a transmissive bio-disc.

FIGS. 3A–3D below illustrate the transmissive disc embodiment of the present invention. Specifically, FIG. 3A shows an exploded perspective view of the principle structural elements of the transmissive type of optical bio-disc 111 similar to the reflective disc 110 of FIGS. 2A–2C. FIG. 3A is an example of a transmissive optical bio-disc 111 (hereinafter, "transmissive disc") that may be used in the present invention. The principle structural elements include the cap portion 116, the adhesive member 118, and the substrate layer 120. The cap portion 116 includes the inlet port 122 and the vent port 124; optionally, may also include a buffer input port 141, similar to that shown in FIG. 2A. The cap portion 116 may be formed from a polycarbonate layer. Optional trigger markings 126 may be included on the surface of cap 116. Trigger markings 126 may include a clear window in all three layers of the bio-disc, an opaque area, or a reflective or semi-reflective area encoded with information that sends data to the processor 166, shown in FIG. 5, which in turn interacts with the operative functions of the interrogation beam 152, FIGS. 3B and 5.

The second element shown in FIG. 3A is the adhesive member 118 having fluidic circuits or U-channels 128 formed therein. The fluidic circuits 128 are formed by stamping or cutting the membrane to remove plastic film and form the shapes as indicated. Each of the fluidic circuits 128 includes the flow channel 130 and the return channel 132. Some of the fluidic circuits 128 illustrated in FIG. 3A include the mixing chamber 134; optionally, they may include a side chamber 139. Two different types of mixing chambers 134 are illustrated. The first is the symmetric mixing chamber 136 which is symmetrically formed relative to the flow channel 130. The second is the off-set mixing chamber 138. The off-set mixing chamber 138 is formed to one side of the flow channel 130 as indicated.

Figure 3B:
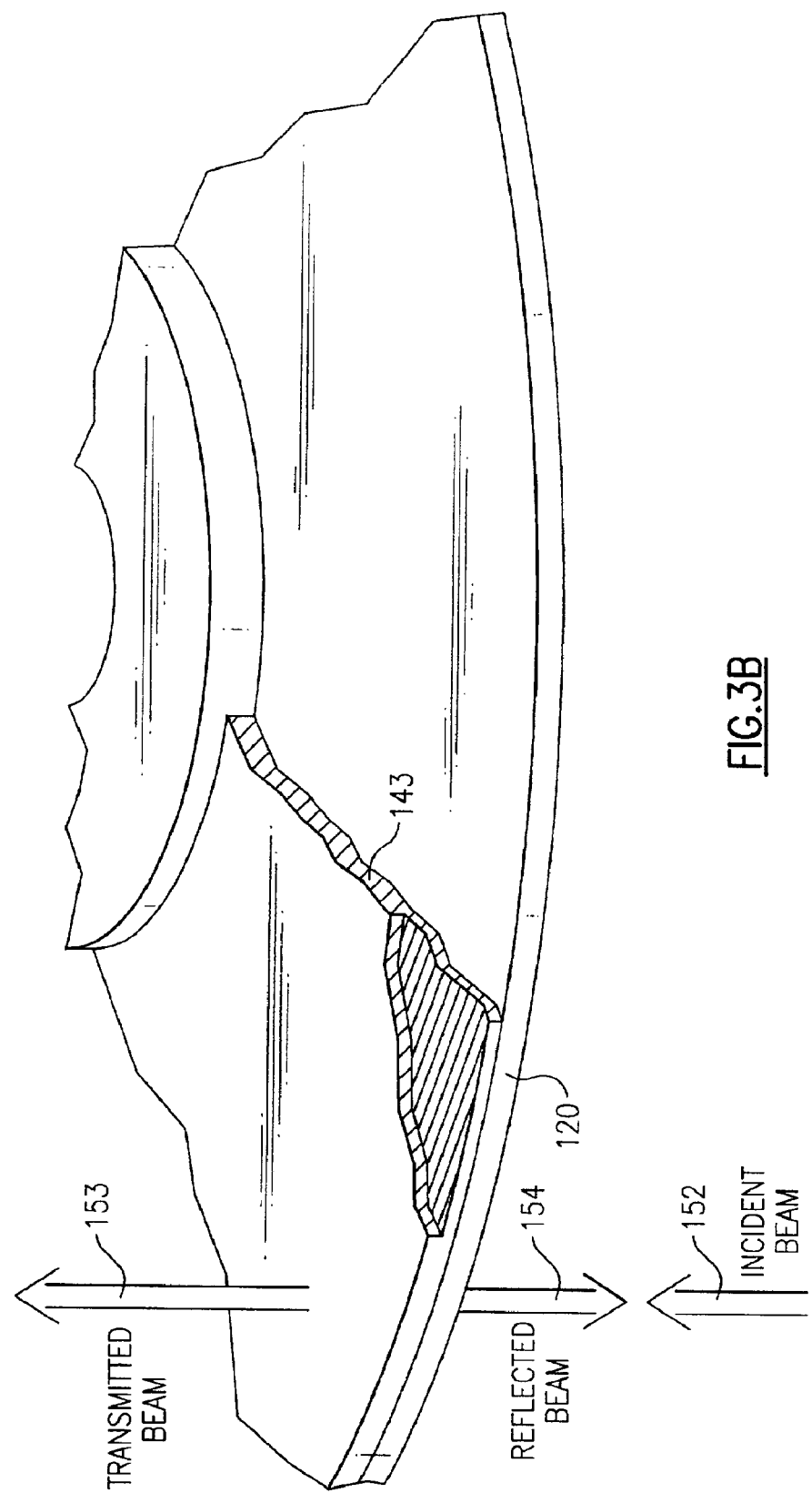
FIG. 3B is an enlarged perspective view of the substrate of the transmissive bio-disc.

The third element illustrated in FIG. 3A is the substrate 120 which may include the target or capture zone 140. The substrate 120 is preferably made of polycarbonate and has the thin semi-reflective layer 143 deposited on the top thereof, as shown in FIG. 3B. The semi-reflective layer 143 on the substrate 120 of FIG. 3B is significantly thinner than the reflective layer 142 on the substrate 120 of FIG. 2C. The thinner semi-reflective layer 143 allows for some transmission of the interrogation beam 152 through the structural layers of the transmissive disc as shown in FIG. 3B. The thin semi-reflective layer 143 may be formed from a metal such as aluminum or gold.

Referring next to FIG. 3B, there is shown an enlarged perspective view of the substrate 120 of the embodiment of the transmissive optical bio-disc 111 illustrated in FIG. 3A. In the preferred embodiment, the thin semi-reflective layer 143 of the transmissive disc illustrated in FIGS. 3B and 3D is approximately 100–300 Angstroms thick and does not exceed 400 Angstroms. This thinner semi-reflective layer 143 allows a portion of the incident or interrogation beam 152 to penetrate and pass through the thin semi-reflective layer 143 to be detected by a top detector 158, shown in FIG. 5, while some of the light is reflected back. Table 1, below, shows the reflective and transmissive characteristics relative to thickness for a gold reflective layer. The gold film layer is fully reflective at a thickness greater than 800 Angstroms, while the threshold density for transmission of light through the gold film is approximately 400 Angstroms.

TABLE 1

| Thickness (Angstroms) | Thickness (nm) | Reflectance | Transmittance |
| --- | --- | --- | --- |
| 0 | 0 | 0.0505 | 0.9495 |
| 50 | 5 | 0.1683 | 0.7709 |
| 100 | 10 | 0.3981 | 0.5169 |
| 150 | 15 | 0.5873 | 0.3264 |
| 200 | 20 | 0.7142 | 0.2057 |
| 250 | 25 | 0.7959 | 0.1314 |
| 300 | 30 | 0.8488 | 0.0851 |
| 350 | 35 | 0.8836 | 0.0557 |
| 400 | 40 | 0.9067 | 0.0368 |
| 450 | 45 | 0.9222 | 0.0244 |
| 500 | 50 | 0.9328 | 0.0163 |
| 550 | 55 | 0.9399 | 0.0109 |
| 600 | 60 | 0.9448 | 0.0073 |
| 650 | 65 | 0.9482 | 0.0049 |
| 700 | 70 | 0.9505 | 0.0033 |
| 750 | 75 | 0.9520 | 0.0022 |
| 800 | 80 | 0.9531 | 0.0015 |

Figure 3C:
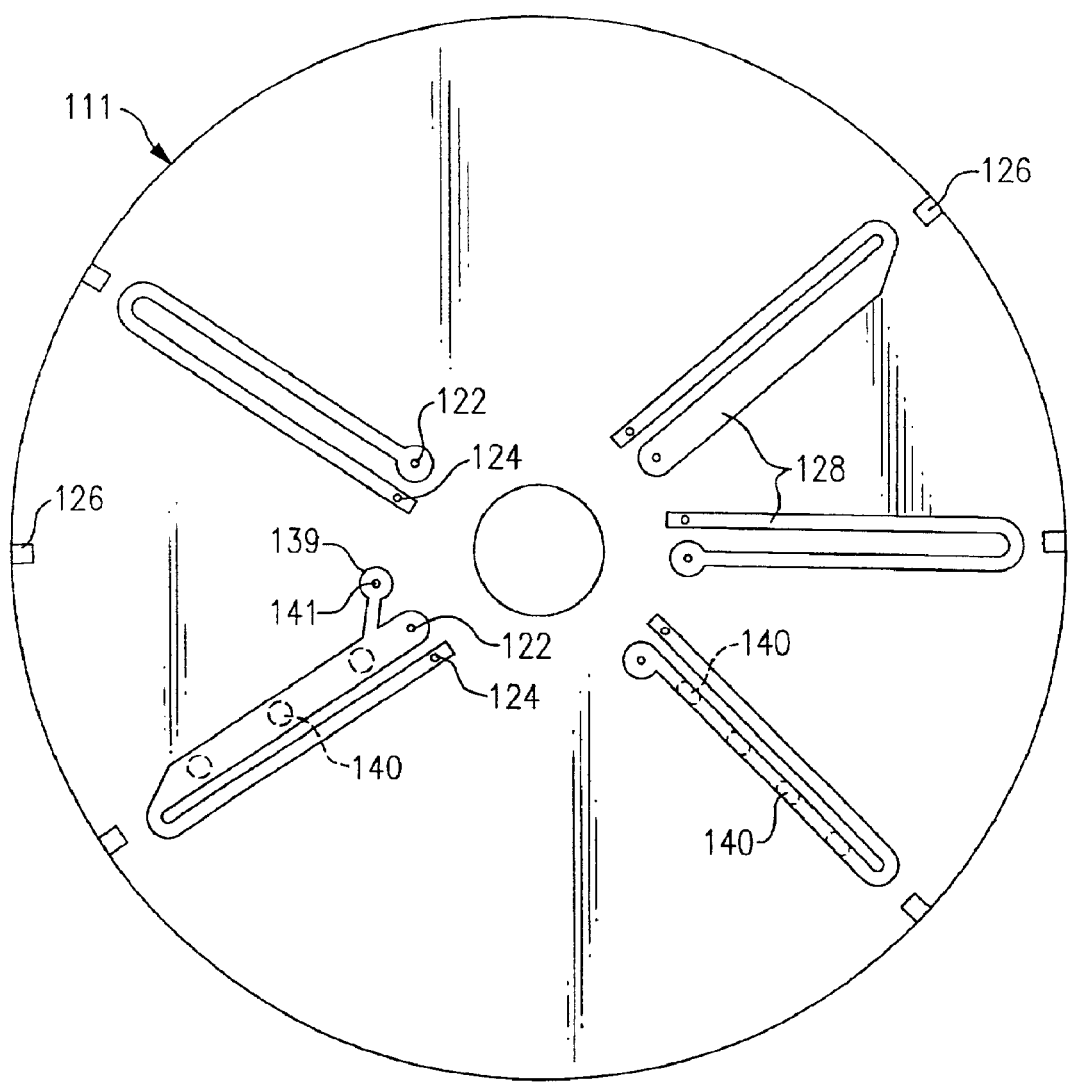
FIG. 3C is a top plan view of the transmissive bio-disc.
Figure 3D:
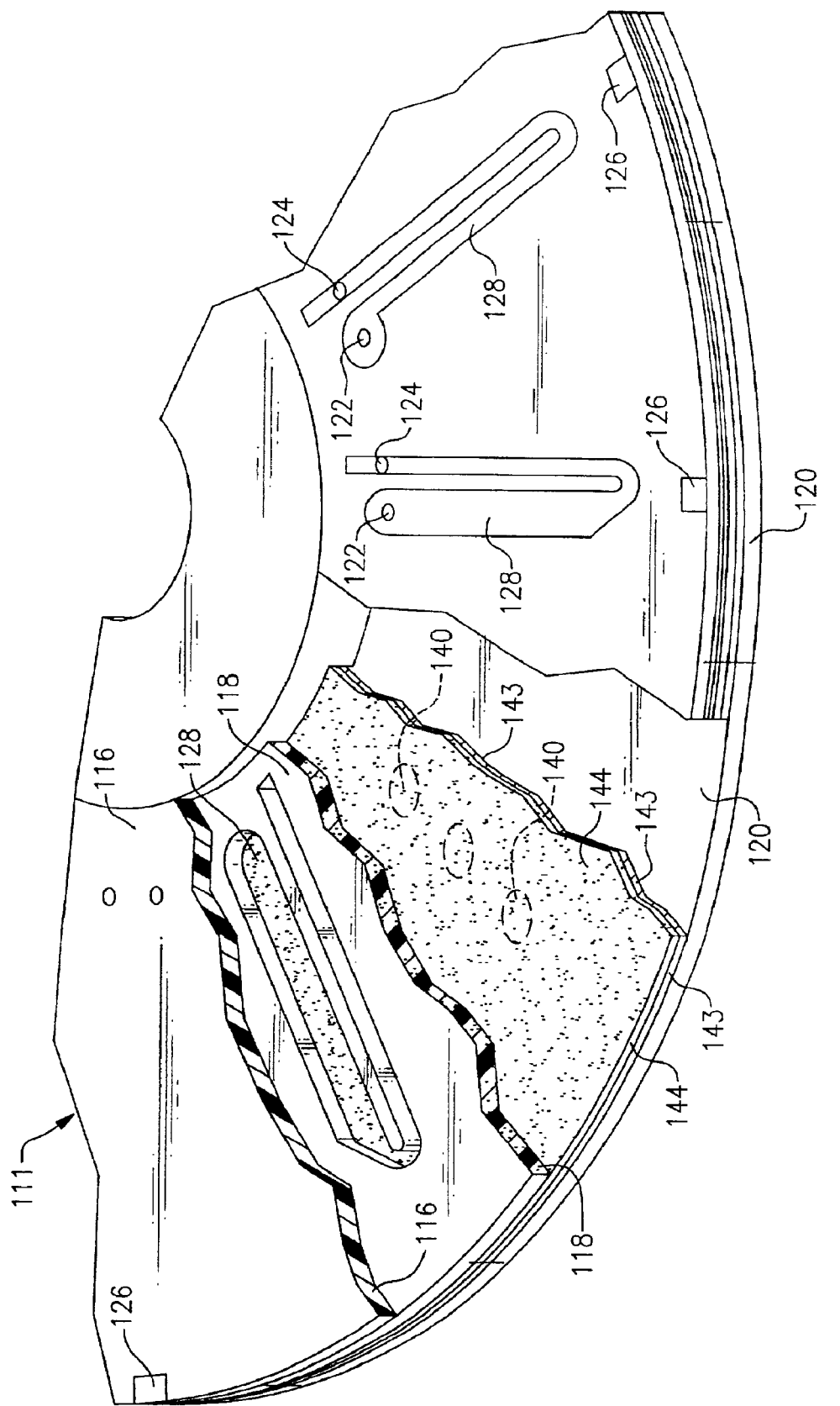
FIG. 3D is an enlarged perspective view of the transmissive bio-disc.

With reference now to FIG. 3C, there is presented a top plan view of the transmissive optical bio-disc 111 illustrated in FIGS. 3A and 3B with the transparent cap portion 116 revealing the fluidic channels 128, the trigger markings 126, and the target or capture zone 140 as situated within the disc. The fluidic circuits 128 may include a side chamber 139 with the buffer input port 141.

Referring next to FIG. 3D, there is illustrated an enlarged perspective view of the transmissive optical bio-disc 111 embodiment of the present invention. The disc 111 is illustrated with a portion of the various layers thereof cut away to illustrate a partial sectional view of each principle, layer, substrate, coating, or membrane. FIG. 3D illustrates the transmissive disc format with the clear cap portion 116, the thin semi-reflective layer 143 on the substrate 120, and trigger markings 126. Trigger markings 126 include opaque material placed on the top portion of the cap, clear, non-reflective windows etched on the thin reflective layer 143 of the disc, or any mark that absorbs or does not reflect the signal coming from the trigger detector 160, shown in FIG. 5.

FIG. 3D also shows target zones 140 formed by marking the designated area in the indicated shape or, alternatively, in any desired shape. Markings to indicate target zone 140 may be made on the thin semi-reflective layer 143 on the substrate 120 or on the bottom portion of the substrate 120 (under the disc). In a preferred embodiment of the present invention, the active layer 144 is formed from nitrocellulose. Alternatively, polystyrene, polycarbonate, gold, activated glass, modified glass, or a modified polystyrene, for example, polystyrene-co-maleic anhydride, may be used.

As illustrated in this embodiment, the plastic adhesive member 118 is applied over the active layer 144. The exposed section of the plastic adhesive member 118 illustrates the cut out or stamped U-shaped form that creates the fluidic circuits 128. The final principle structural layer in this embodiment of the present bio-disc 110 is the clear, non-reflective cap portion 116 that includes the inlet 122, vent port 124, and, optionally, the buffer port (not shown) as described above in FIG. 3C.

Figure 4:
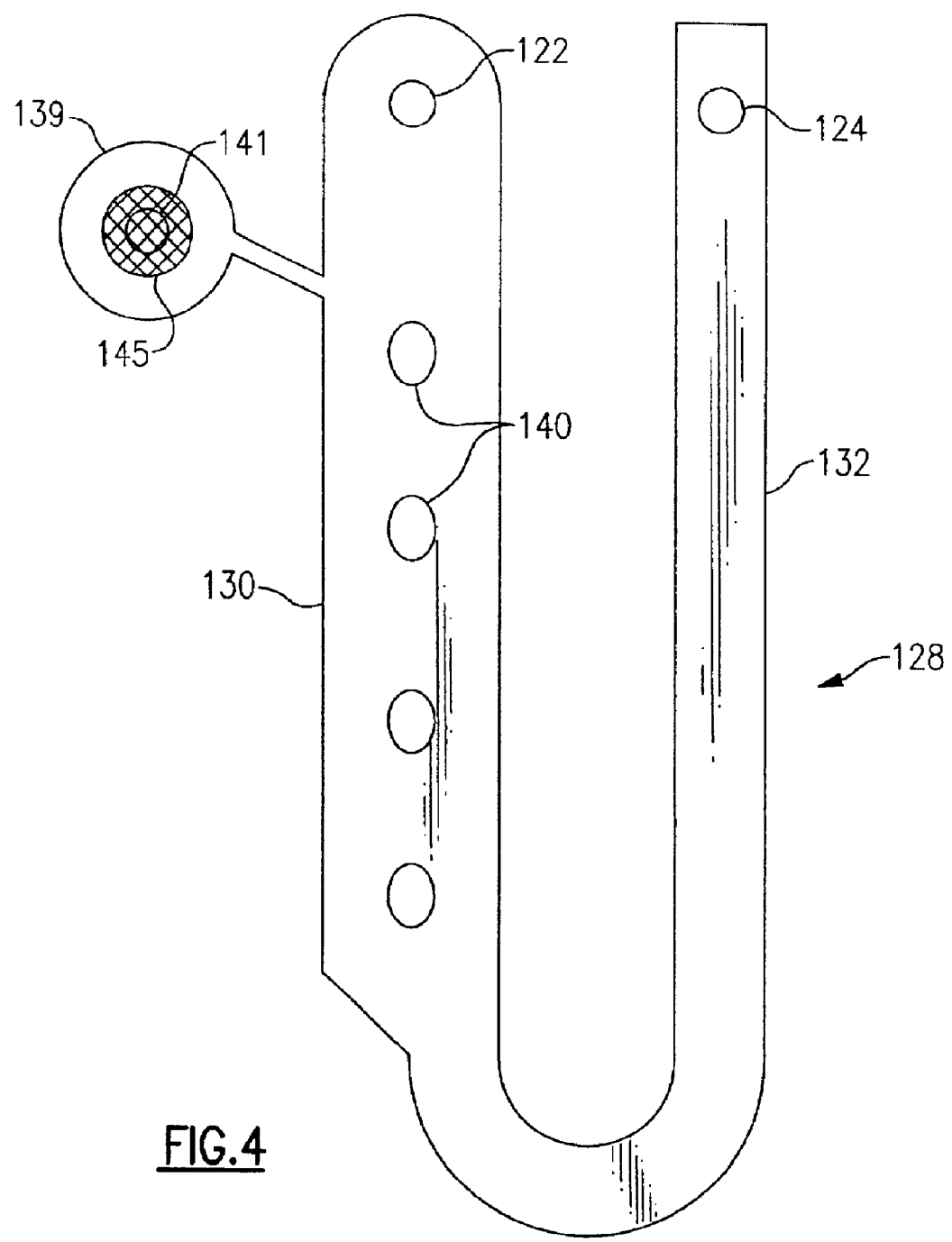
FIG. 4 is an enlarged top plan view of an alternative embodiment of a fluidic circuit having a side chamber.

Referring now to FIG. 4, there is illustrated an enlarged top plan view of a fluidic circuit 128 of the reflective disc 110 or transmissive disc 111 having a side chamber 139, the buffer inlet port 141, and the target zones 140 situated within the disc. In this embodiment, a membrane or pad 145, onto which conjugated enzyme may be dried on, is deposited in the side chamber 139. In this embodiment, an enzyme buffer is added to the side chamber 139 via a buffer inlet port 141 to solubilize the enzyme, which then enters the flow channel 130 where it can interact with the biotinylated target DNA or signal DNA bound within the target zones 140.

With reference now to FIG. 5, there is a representation in perspective and block diagram the optical bio-disc system showing optical components 148, a light source 150 that produces an incident or interrogation beam 152, a return beam 154, and a transmitted beam 156. In the case of the reflective bio-disc, the return beam 154 is reflected from the cap portion 116 of the reflective bio-disc 110. In this embodiment of the present invention, the return beam 154 is detected and analyzed for the presence of signal agents by a bottom detector 157.

In the transmissive bio-disc 111, on the other hand, the transmitted beam 156 is detected by a top detector 158 and is analyzed for the presence of signal agents. In this embodiment, a photo detector may be used as a top detector 158.

FIG. 5 also shows a hardware trigger mechanism that includes the trigger markings 126 on the disc and a trigger detector 160. The hardware triggering mechanism is used in both reflective bio-discs 110 (FIG. 2C) and transmissive bio-discs 111 (FIG. 3D). The triggering mechanism allows the processor 166 to collect data only when the interrogation beam 152 is on a respective target zone. Alternatively, a software triggering system may also be used to control the data acquisition parameters. The software trigger uses the bottom detector to signal the processor 166 to collect data as soon as the interrogation beam 152 hits the edge of a respective target zone 140 or fluidic circuit 130. Further details relating to triggering methods, data aquistion, and disc drive mechanisms in optical disc systems is disclosed in, for example, commonly assigned co-pending U.S. patent application Ser. No. 10/043,688, entitled "Optical Disc Analysis System Including Related Methods For Biological and Medical Imaging" filed Jan. 10, 2002, which is incorporated herein by reference in its entirety.

FIG. 5 also illustrates a drive motor 162 and a controller 164 for controlling the rotation of the optical bio-disc 110 or 111. FIG. 5 further illustrates the processor 166 and analyzer 168 implemented for processing the return 154 and transmitted beams 156.

Figure 6:
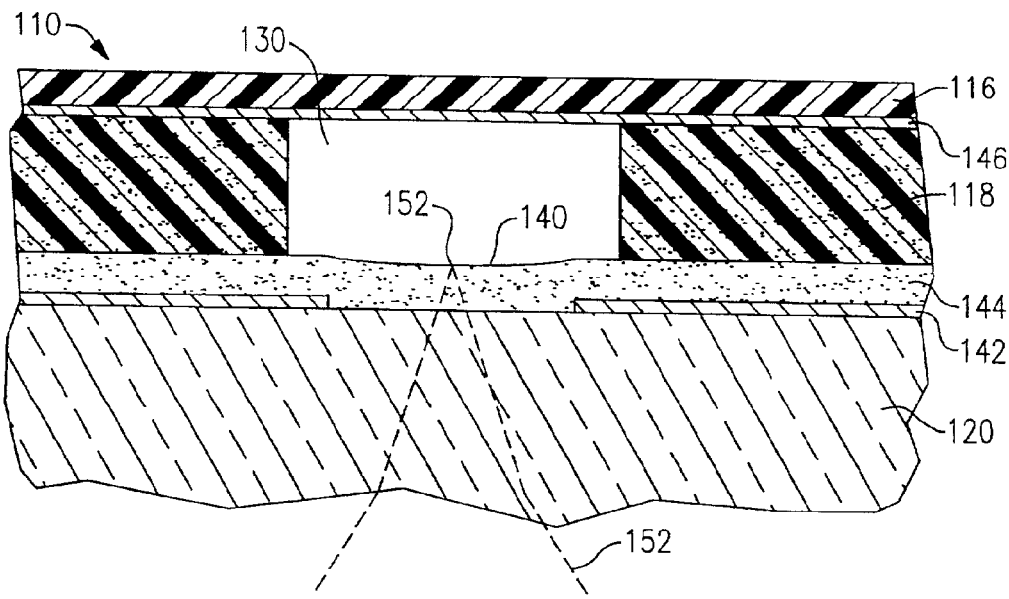
FIG. 6 is a cross sectional view of a reflective bio-disc.

Referring now to FIG. 6, there is shown a cross sectional view of one embodiment of the reflective optical bio-disc 110 according to the present invention. FIG. 6 also shows the substrate 120 and the reflective layer 142. In this embodiment, the substrate 120 is smooth. FIG. 6 also illustrates the active layer 144 applied over the reflective layer 142. As shown in FIG. 6, the target zone 140 is formed by removing an area or portion of the reflective layer 142 at a desired location or, alternatively, by masking the desired area prior to applying the reflective layer 142. As further illustrated in FIG. 6, the plastic adhesive member 118 is applied over the active layer 144. FIG. 6 also shows the cap portion 116 and the reflective surface 146 associated therewith. Thus when the cap portion 116 is applied to the plastic adhesive member 118 including the desired cut-out shapes, the flow channel 130 is thereby formed.

Figure 7:
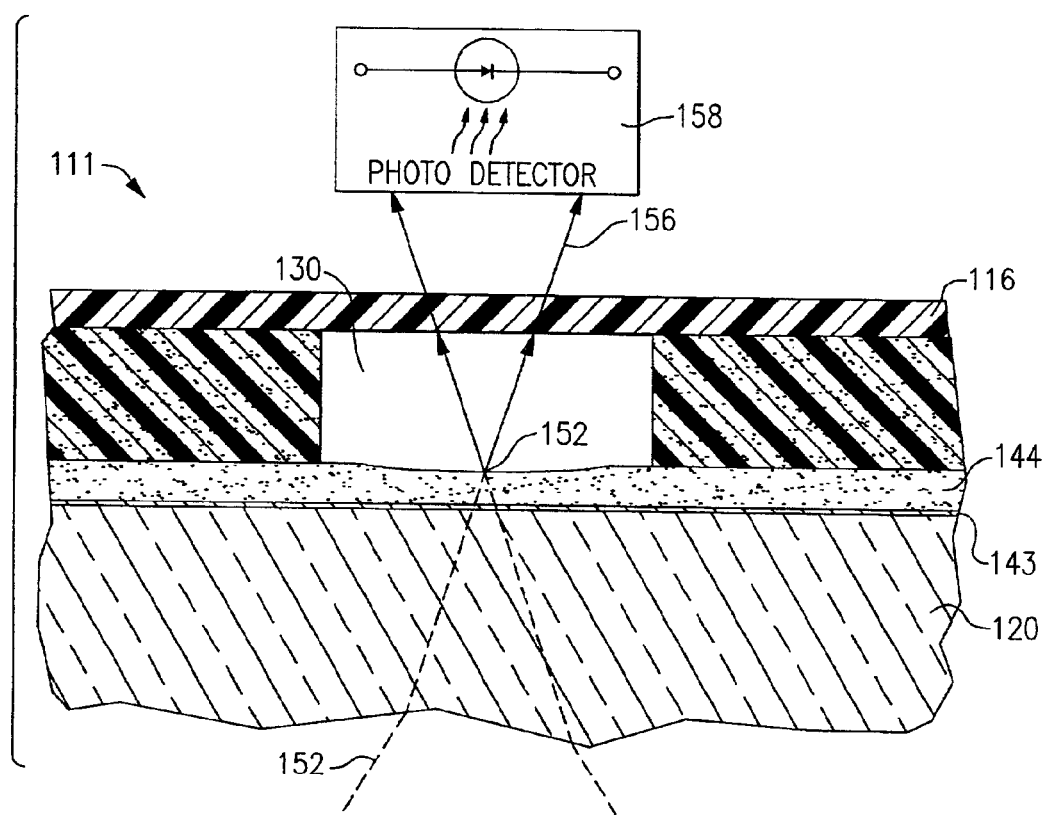
FIG. 7 is a cross sectional view of a transmissive bio-disc.

Reference in now made to FIG. 7 that shows a cross sectional view of an embodiment of the transmissive bio-disc 111 according to the present invention. FIG. 7 illustrates the clear cap portion 116 and the thin semi-reflective layer 143 on the substrate 120 of the transmissive disc 111. The substrate 120 in this embodiment is smooth. FIG. 7 also shows the active layer 144 applied over the thin semi-reflective layer 143. In the preferred embodiment, the transmissive disc has the thin semi-reflective layer 143 made from a metal such as aluminum or gold, approximately 100 to 300 Angstroms thick, not exceeding 400 Angstroms. This thin semi-reflective layer 143 allows some portion of the incident or interrogation beam 152 to penetrate and pass through the disc to be detected by a top detector 158, while some portion of the light is reflected back along the same path as the incident beam but in the opposite direction as described above. The reflected light or return beam is used for tracking of the light source along the disc. In the disc embodiment illustrated in FIG. 7, a defined target zone 140 may or may not be present. Target zone 140 may be created by direct markings made on the thin semi-reflective layer 143 on the substrate 120. These marking may be done using silk screening or any equivalent method.

Figure 8:
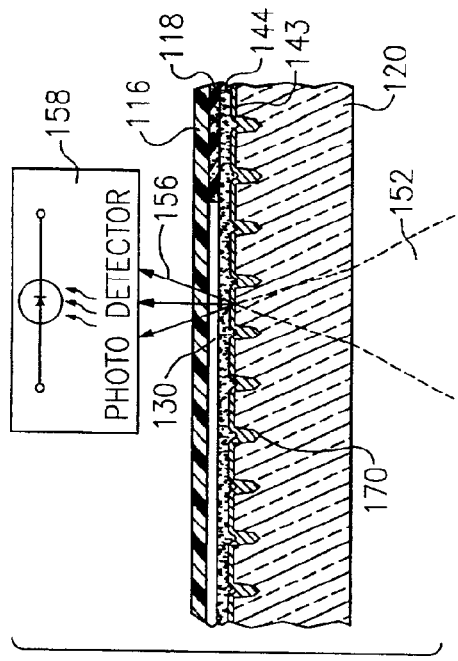
FIG. 8 is a cross sectional view taken across the tracks of the reflective bio-disc embodiment.

With reference now to FIG. 8, there is illustrated a cross sectional view taken across the tracks of the reflective disc 110 embodiment of the bio-disc according to the present invention. FIG. 8 includes the substrate 120 and the reflective layer 142. The substrate 120 in this embodiment includes a series of grooves 170. The grooves 170 are in the form of a spiral extending from near the center of the disc toward the outer edge. The grooves 170 are implemented so that the interrogation beam 152 may track along the spiral grooves 170 on the disc. This type of groove 170 is known as a "wobble groove." The groove 170 is formed by a bottom portion having undulating or wavy side walls. A raised or elevated portion separates adjacent grooves 170 in the spiral. The reflective layer 142 applied over the grooves 170 in this embodiment is, as illustrated, conformal in nature.

FIG. 8 also shows the active layer 144 applied over the reflective layer 142. As shown in FIG. 8, the target zone 140 is formed by removing an area or portion of the reflective layer 142 at a desired location or, alternatively, by masking the desired area prior to applying the reflective layer 142. As further illustrated in FIG. 8, the plastic adhesive member 118 is applied over the active layer 144. FIG. 8 also shows the cap portion 116 and the reflective surface 146 associated therewith. Thus, when the cap portion 116 is applied to the plastic adhesive member 118 including the desired cut-out shapes, the flow channel 130 is thereby formed.

Figure 9:
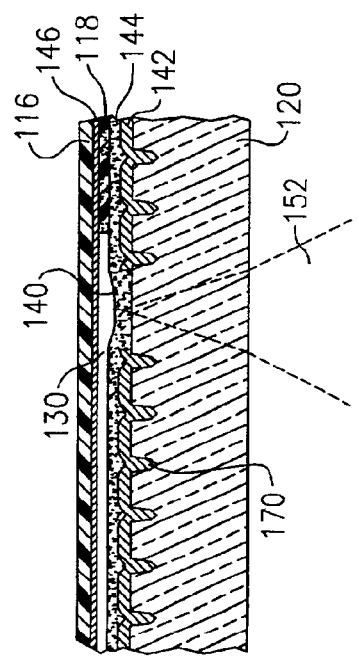
FIG. 9 is a cross sectional view taken across the tracks of the transmissive bio-disc embodiment.

Referring to FIG. 9, there is depicted a cross sectional view taken across the tracks of the transmissive disc 111 embodiment, as described above in conjunction with FIG. 7. FIG. 9 illustrates the substrate 120 and the thin semi-reflective layer 143. In the preferred embodiment, the transmissive disc has the thin semi-reflective layer 143 made from a metal such as aluminum or gold, which is approximately 100 to 300 Angstroms thick and does not exceed 400 Angstroms. This thin semi-reflective layer 143 allows the incident or interrogation beam 152 to penetrate and pass through the disc (transmitted beam 156) to be detected by the top detector 158, while some of the light is reflected back. The thickness of the thin semi-reflective layer 143 is determined by the minimum amount of reflected light required by the disc reader to maintain its tracking ability.

The substrate 120 in this embodiment includes a series of grooves 170. The grooves 170 are in the form of a spiral extending from near the center of the disc toward the outer edge and are implemented so that the interrogation beam 152 may track along the spiral.

FIG. 9 also shows the active layer 144 applied over the thin semi-reflective layer 143. As further illustrated in FIG. 9, the plastic adhesive member 118 is applied over the active layer 144. FIG. 9 also shows the cap portion 116 without a reflective surface. Thus, when the cap is applied to the plastic adhesive member 118 including the desired cut-out shapes, the flow channel 130 is thereby formed and the incident beam is allowed to pass therethrough substantially unreflected.

Figure 10:
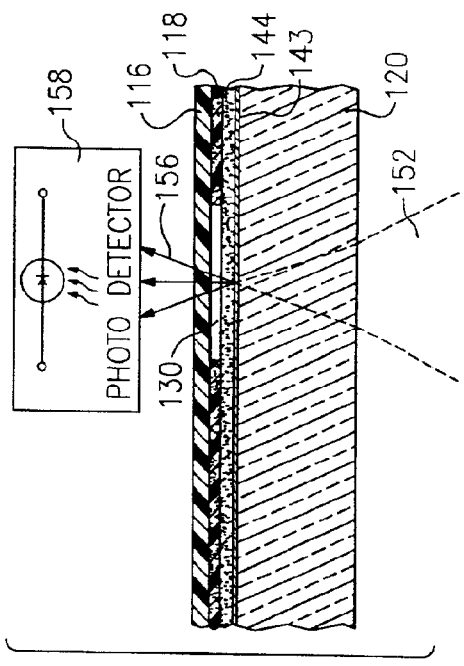
FIG. 10 is a longitudinal cross-section of the reflective bio-disc embodiment shown in FIG. 8.
Figure 11:
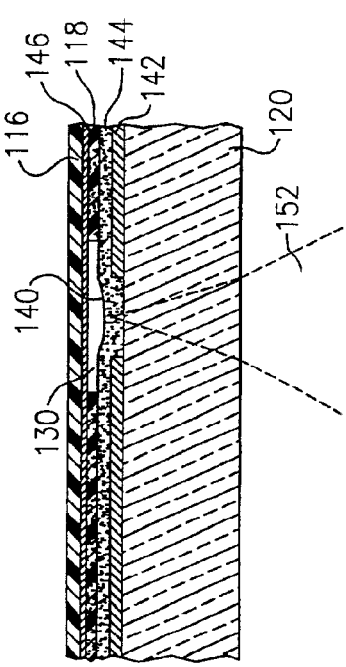
FIG. 11 is a longitudinal cross-section of the transmissive bio-disc embodiment shown in FIG. 9.

FIGS. 10 and 11 shows longitudinal cross-sections of the embodiments shown in FIGS. 8 and 9, respectively, containing all components mentioned in FIGS. 8 and 9. Grooves 170 are not seen in this illustration since the sections are cut along the grooves 170. This section also shows the presence of the narrow flow channels 130 that are perpendicular to the grooves 170.

Open Disc Formats

Referring to FIG. 12, there is illustrated an embodiment of the present optical bio-disc 110 that utilizes a reflective open-face or open-disc format. In this embodiment, the substrate 120 is implemented as a distal layer relative to the interrogation beam 152. The reflective layer 142, showing tracking grooves 170, is next provided as illustrated. The bottom layer or proximal layer relative to the beam in this embodiment is provided by the active layer 144.

In this embodiment, a capture DNA 172 may be depended downwardly when the disc is loaded in the drive (FIG. 1). In this open-face format, the other assay reactants are brought into proximity with the capture DNA 172 by a variety of different methods which include, for example, depositing a test sample on the disc with a pipette. In this embodiment, the target zones 140 are simply formed by the application of a small volume of capture DNA 172 solution to the active layer 144 to form clusters of capture DNA 172 in desired locations on the active layer 144 as illustrated.

Referring next to FIG. 13, there is shown an alternate embodiment of the open-face or open-disc optical bio-disc. In this transmissive disc 111 embodiment, the substrate 120 is implemented as a proximal layer relative to the interrogation beam 152. The thin semi-reflective layer 143, showing tracking grooves 170, is next provided as illustrated. The thin semi-reflective layer 143 is relatively thinner than the reflective layer 142 described in FIG. 12 to allow transmission of some desired percentage of the incident beam, while some portion is reflected back to facilitate tracking on the disc. Detection of the transmitted beam 156 is then carried out by the top detector 158 as discussed above in conjunction with FIGS. 5 and 7. The top layer or distal layer relative to the interrogation beam in this embodiment is provided by the active layer 144. In this embodiment, the capture DNA 172 may be oriented upward when the disc is loaded in the drive (FIG. 1).

In this transmissive (or semi-reflective) open-face format, the assay reactants are brought into proximity with the capture DNA 172 by a variety of different methods which include, for example, depositing a test sample on the disc with a pipette. In this alternative embodiment, the target zones 140 are simply formed by the application of a small volume of capture DNA 172 solution to the active layer 144 to form clusters of capture DNA 172 in desired locations on the active layer 144 as illustrated. Detection of the beam carrying information about the analyte for this embodiment is achieved by use of a top detector 158.

FIGS. 14 and 15 show longitudinal cross-sections of the embodiments shown in FIGS. 12 and 13, respectively, containing all components mentioned in FIGS. 12 and 13. Grooves 170 are not seen in this illustration since the sections are cut along the grooves 170.

Attaching Capture DNA, Target DNA, and Conjugated Enzyme

Figure 16:
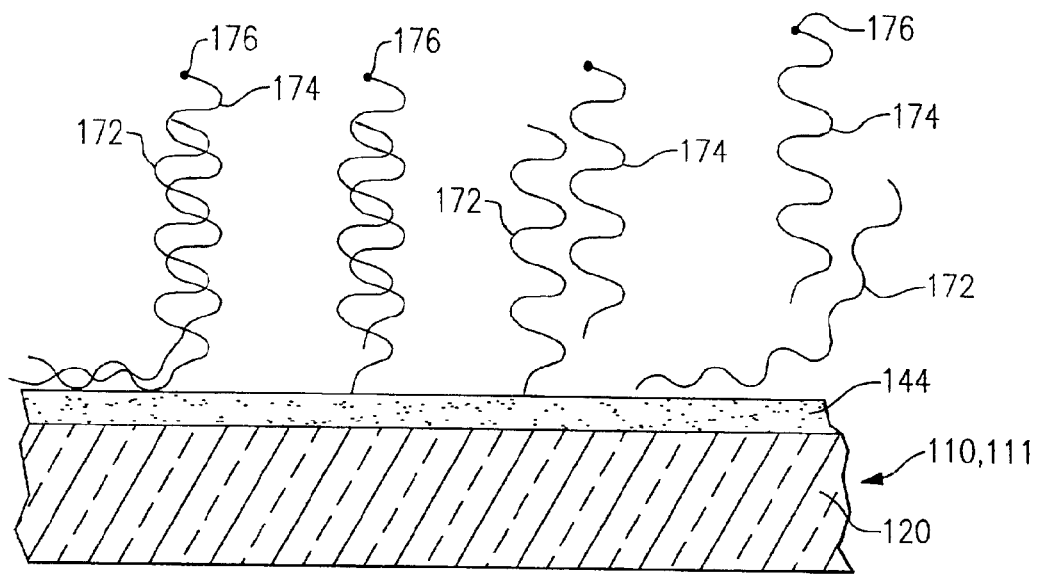
FIG. 16 is an enlarged detailed partial cross sectional view showing the active layer and the substrate of the bio-disc, with capture DNA and target DNA.

Referring to FIG. 16, there is portrayed an enlarged detailed partial cross sectional view showing the active layer 144 and the substrate 120 of the present bio-disc 110 or 111. FIG. 16 also illustrates the capture DNA 172 attached to the active layer 144 in the target zone. In this embodiment, the capture DNA 172 binds onto the active layer 144 through passive adhesion. However, the capture DNA 172 may also be bound to the active layer by covalent binding as discussed above. As indicated, the capture DNA 172 is situated within the target zone. The bond between the capture DNA 172 and the active layer 144 is sufficient so that the capture DNA 172 remains attached to the active layer 144 within the target zone 140 when the disc is rotated.

FIG. 16 also depicts the target DNA 174. In this embodiment of the present invention, the target DNA 174 includes an affinity agent 176, such as, for example, biotin. The capture DNA is selected such that a portion of the capture DNA sequence is complementary to a potion of the sequence of the target DNA, allowing hybridization between the capture and target DNA as the target DNA flows toward the capture DNA 172 as shown.

Figure 17:
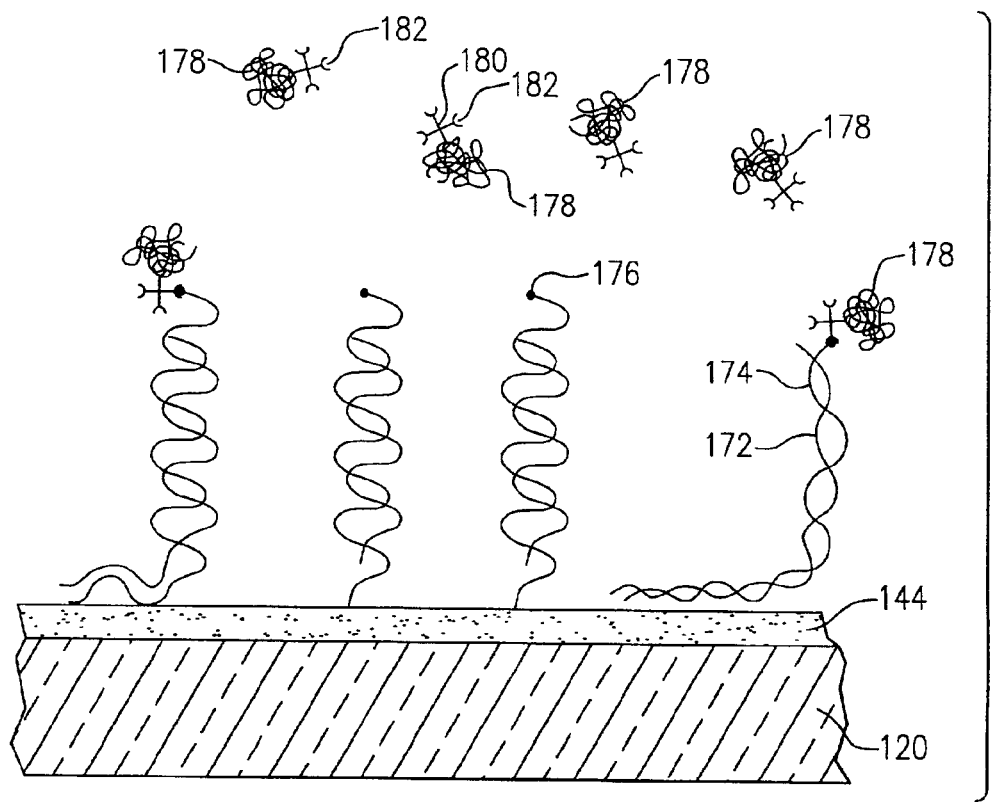
FIG. 17 is an enlarged view similar to FIG. 16, shown after the introduction of enzymes.

Referring next to FIG. 17, there is shown an enlarged view similar to FIG. 16, showing the introduction of enzymes 178. As illustrated in FIG. 17, the enzymes 178 are conjugated with a binding agent 180 that includes receptors 182. The binding agent 180 includes streptavidin, neutravidin and the like. In this embodiment of the present invention, the target DNA 174 hybridizes with capture DNA 172 and the affinity agent 176 links with the receptor 182 of the binding agent 180 to anchor the enzyme within the target zone.

Figure 18:
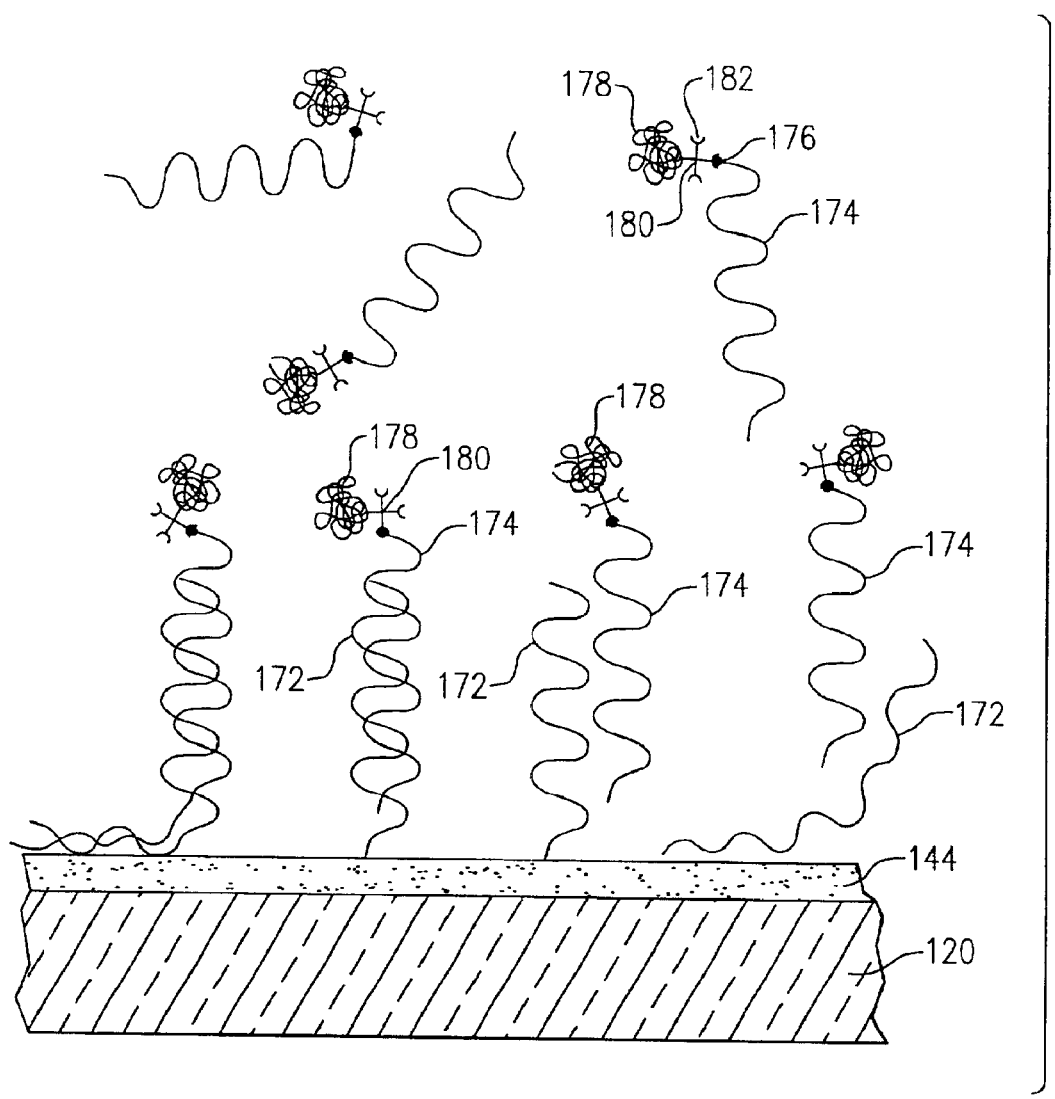
FIG. 18 is an enlarged detailed partial cross sectional view showing an alternate method of introducing the target DNA, in which the enzyme is pre-conjugated to the target DNA.

Referring now to FIG. 18, there is shown an alternate method of introducing the enzyme 178. FIG. 18 illustrates the enzyme pre-conjugated to the target DNA 174 via interaction between an affinity agent 176, such as biotin, on the target DNA and a binding agent 180, conjugated to the enzyme 178. The binding agent 180 includes affinity agent 176. The binding agent 180 may be, for example, streptavidin or neutravidin. In this embodiment, the pre-conjugated enzyme-DNA complex hybridizes directly to the capture DNA probes, which are attached to the active layer 144 in the target zone thereby imobilize the enzyme within the target zone.

Using a Signal DNA to Attach Conjugated Enzyme to the Target Zone

Figure 19:
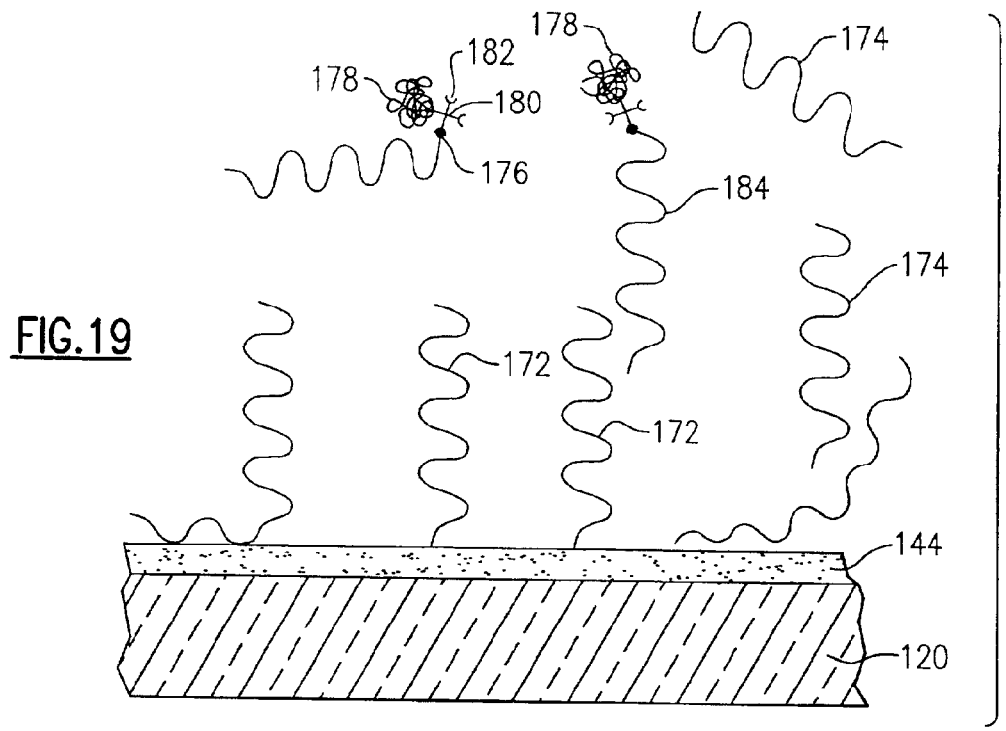
FIG. 19 is a detailed partial cross sectional view showing the active layer and the substrate of the present bio-disc according to an embodiment utilizing a signal DNA attached to enzymes.
Figure 20:
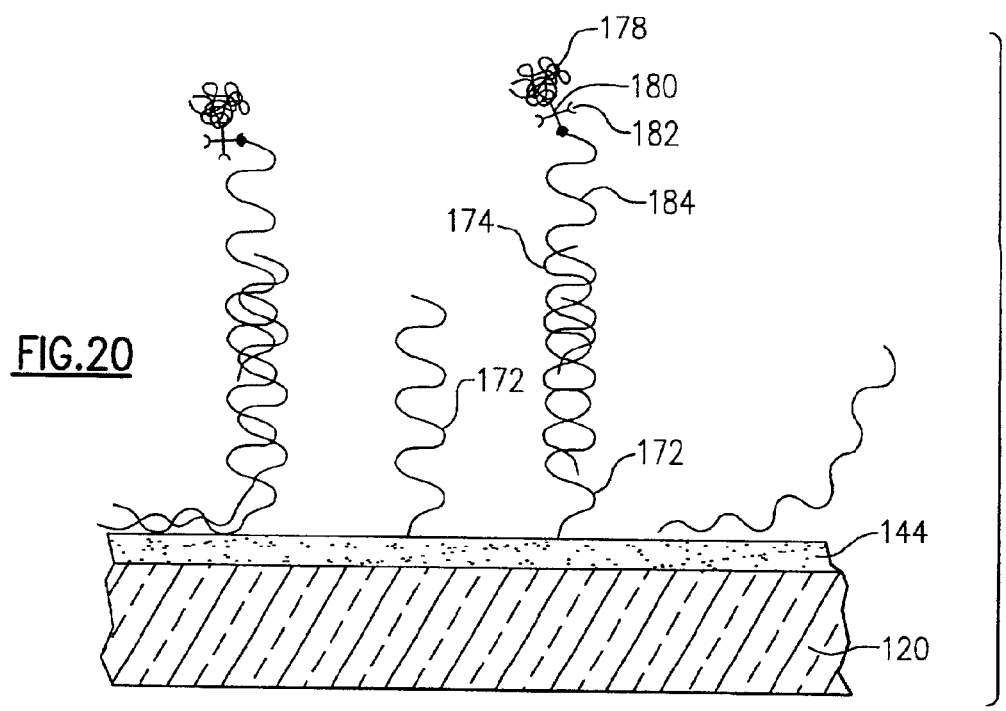
FIG. 20 is a detailed partial cross sectional view similar to FIG. 19, showing the signal DNA/target DNA or RNA/capture DNA complex formed at the target zone, with bound enzymes.

With reference to FIG. 19, there is illustrated a detailed partial cross sectional view showing the active layer 144 and the substrate 120 of the present bio-disc according to the embodiment utilizing the enzyme 178 attached to a signal DNA 184. In this embodiment, biotinylated signal DNA 184 is linked to the enzyme 178 via the binding agent 180 and the receptors 182 associated therewith. In this method, the signal DNA 184 is non-complementary to the capture DNA 172, while the target RNA or DNA 174 contains separate sequences that are complementary to the signal DNA 184 and the capture DNA 172. In this embodiment, the target RNA or DNA 174 acts as a "bridge" to attach the signal DNA 184 to the capture DNA 172, as shown in FIG. 20. This places the enzymes 178 in the target zone when the target RNA or DNA 174 is present. In this embodiment, the signal DNA 184 may be pre-conjugated with the enzyme prior to hybridizing with the target DNA. Alternatively, biotinylated signal DNA can be hybridized to the target DNA first, then exposed to the conjugated enzyme.

The Enzyme-Substrate Reaction and the Formation of an Insoluble Precipitate

Figure 21:
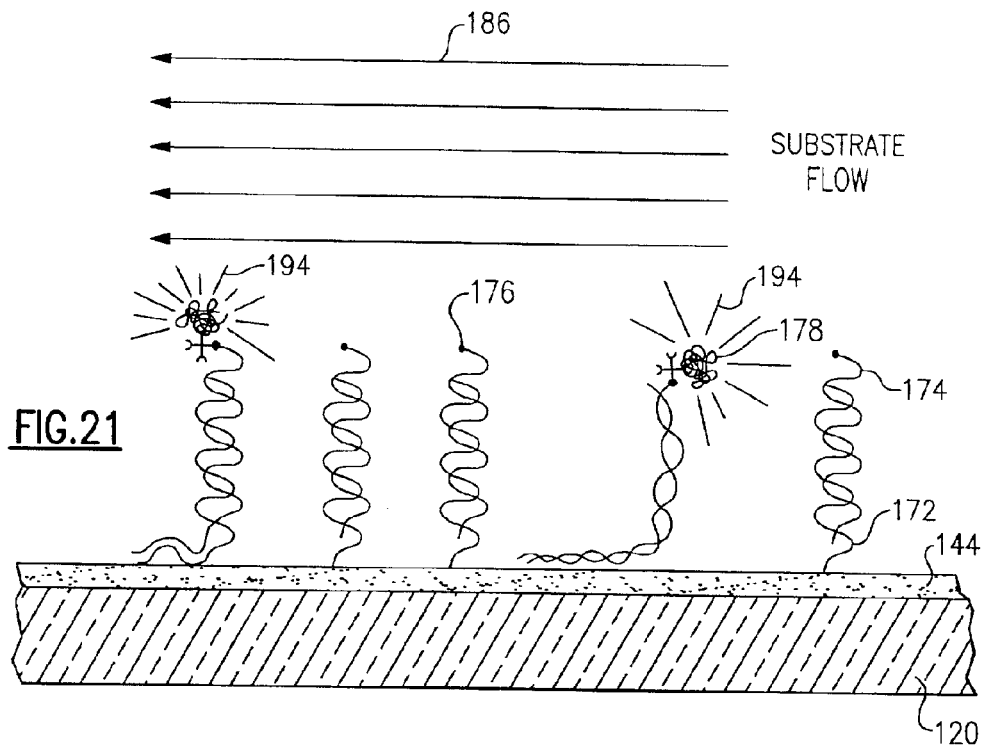
FIG. 21 is a detailed partial cross sectional view of a reaction, showing the active layer, the substrate, target RNA or DNA 174 hybridized to the capture DNA, and the introduction of enzyme substrate, resulting in enzyme/substrate reactions by enzymes bound to the target DNA or RNA.

Referring to FIG. 21, there is shown a detailed partial cross sectional view of a target zone including the active layer 144, the substrate 120, and target RNA or DNA 174 hybridized to the capture DNA 172. The target RNA or DNA 174 may contain an affinity agent 176 such as biotin; alternatively, the target nucleic acid can be hybridized to a signal DNA 184 with an affinity agent 176. Thus, the enzyme 178 may be attached directly to the target RNA or DNA 174 or to signal DNA 184 as described in FIGS. 16–20. FIG. 21 also shows the addition of an enzyme substrate 186. Enzyme-substrate reaction 194 occurs as soon as the substrate comes in contact with the enzyme 178. The resulting enzyme-substrate reaction 194 produces a signal that is detectable by a disc type reader. The signal generated may consist of precipitate formation, enzyme substrate luminescence, and/or enzyme substrate color change or formation.

FIGS. 22A–22D illustrate a method according to the present invention for detecting or determining the presence of target RNA or DNA 174 in a sample by precipitate formation through an enzyme-substrate reaction 194 in conjunction with the optical bio-discs 110 or 111 according to the present invention. FIGS. 22A–22D are detailed partial cross sectional views of a target zone showing the active layer 144, the substrate 120, and target RNA or DNA 174 hybridized to the capture DNA 172. The target RNA or DNA 174 may contain an affinity agent 176 or, alternatively, can be hybridized to a signal DNA containing an affinity agent. The enzyme can then be attached to either the target RNA or DNA 174 or signal DNA 184 as described above in conjunction with FIGS. 16–20.

Figure 22A:
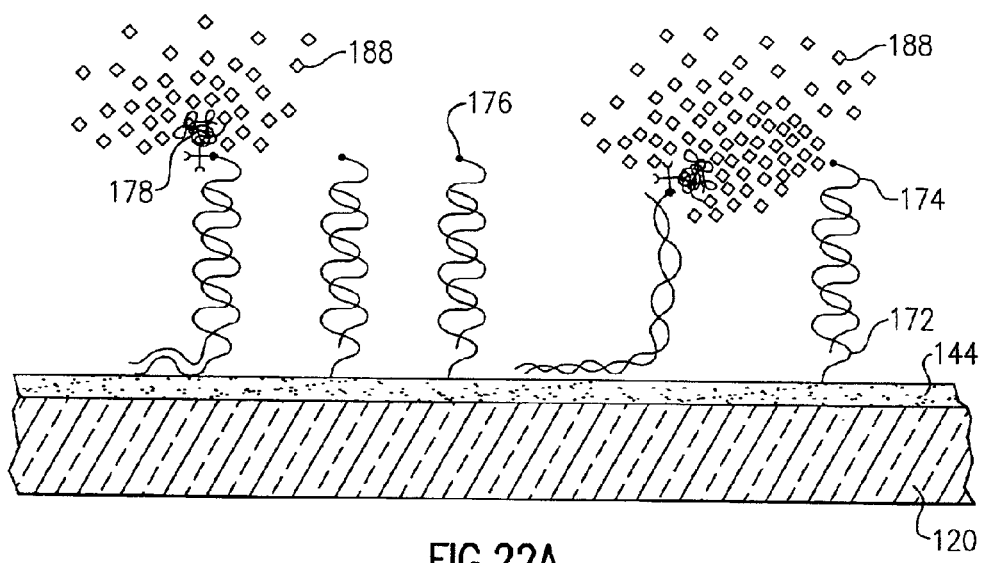
FIGS. 22A–22D are detailed partial cross sectional views of a target zone showing a method according to the present invention for detecting or determining the presence of target RNA or DNA in a sample by pellet formation through an enzyme-substrate reaction in conjunction with the optical bio-disc.
Figure 22B:
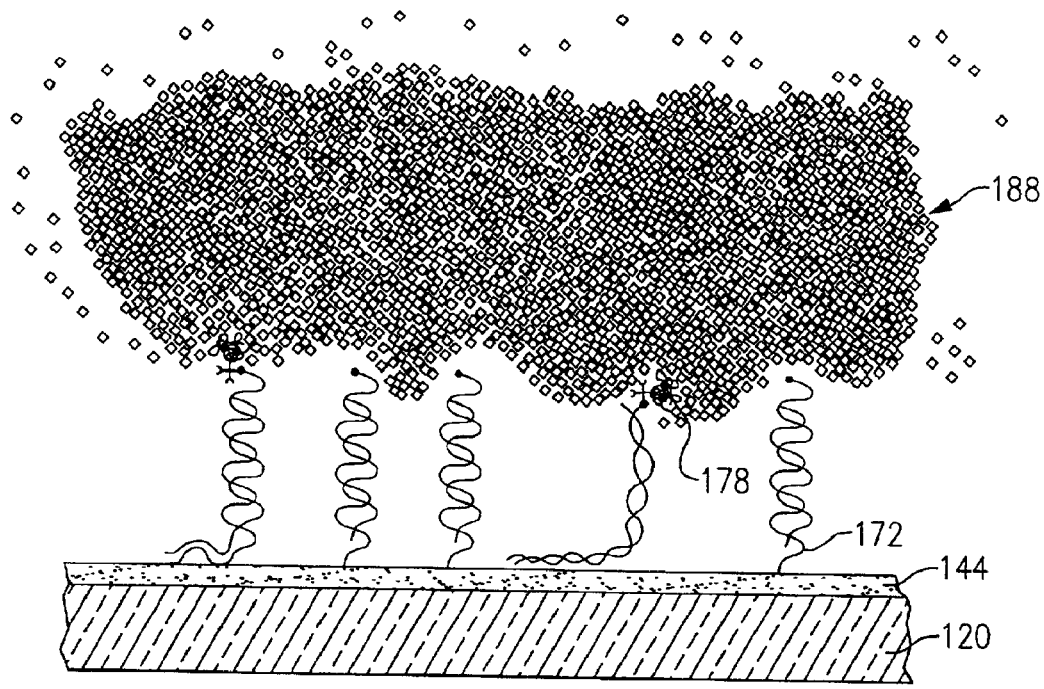

Referring now to FIG. 22A, there is depicted the formation of an insoluble product 188 by the enzyme-substrate reaction 194 (FIG. 21). FIG. 22B further illustrates more massive amounts of insoluble product 188 formed by the enzyme reaction, which fill the capture or target zone.

Figure 22C:
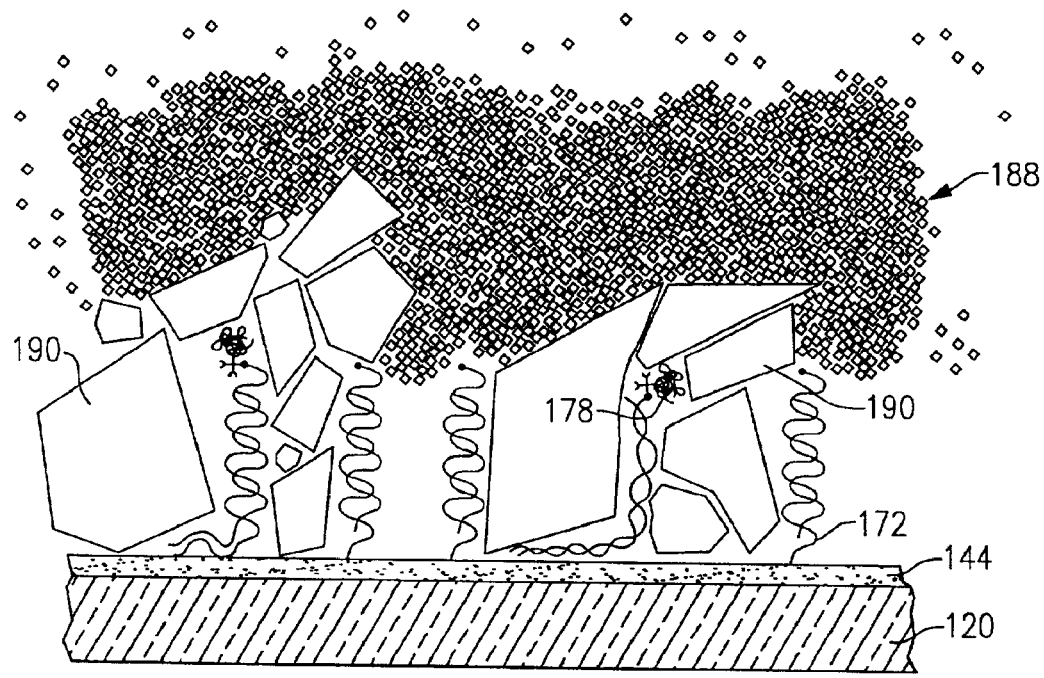

Referring next to FIG. 22C, there is shown the insoluble product 188 aggregating and forming insoluble pellets or precipitates 190, which are deposited within the target zone. The active layer 144 may facilitate aggregation and deposition of the insoluble products 188, resulting in the formation of pellets comprising precipitates 190 that adhere to the active layer.

Figure 22D:
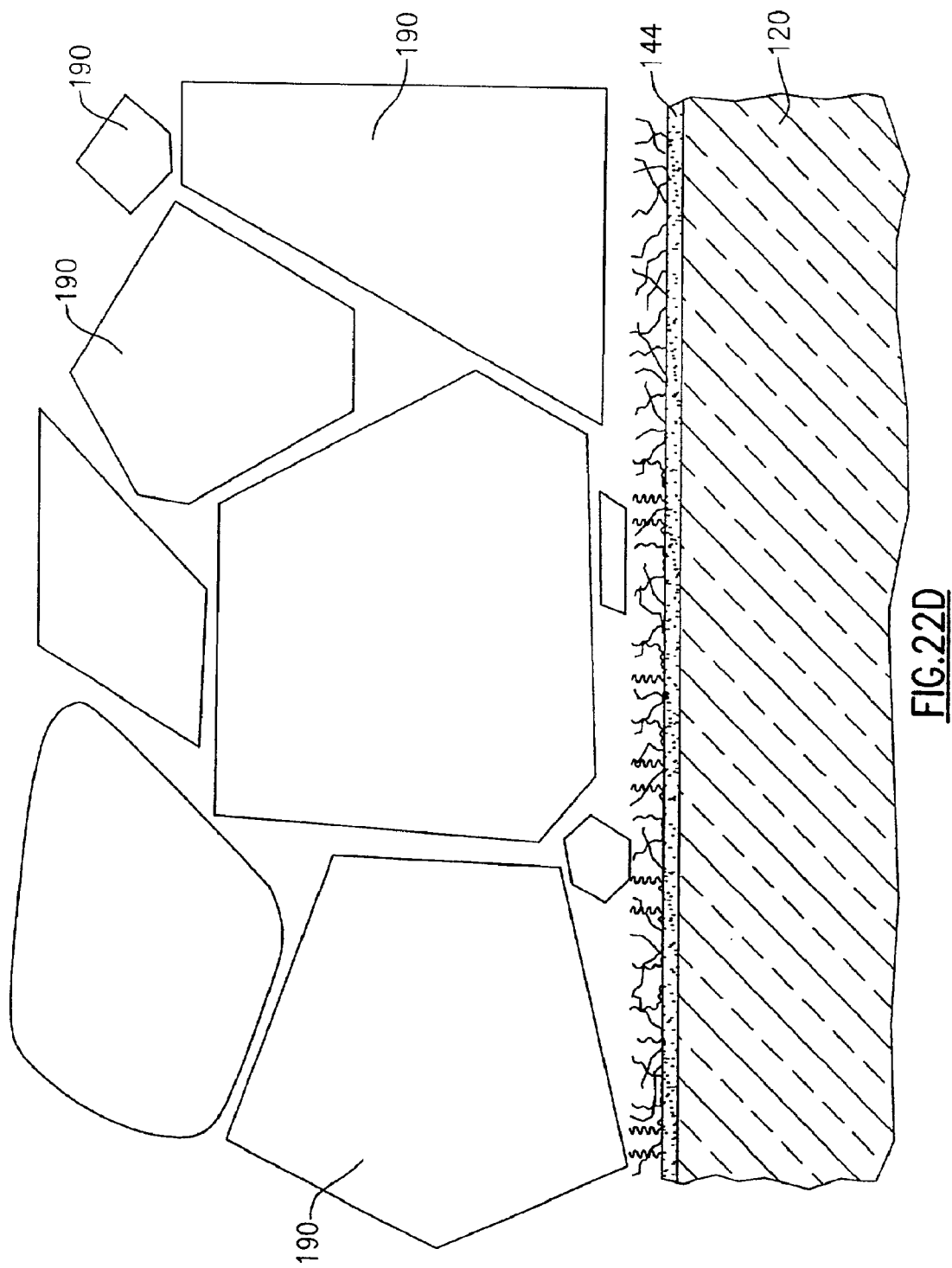

Next, FIG. 22D shows an expanded view of the complete aggregation of the insoluble product 188 forming large precipitate particles 190, relative to the DNA deposited on the target zone. These large aggregated particles or pellets 190 can then be detected using a disc reader.

Target Detection Methods

Figure 23:
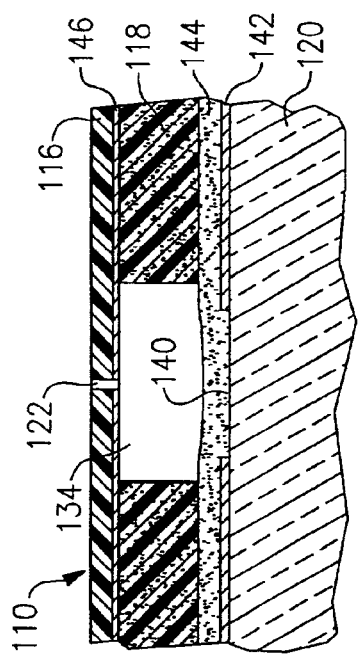
FIG. 23 is a longitudinal cross sectional view (cut along the tracking grooves) of the mixing chamber of the reflective bio-disc showing the inlet port.

FIG. 23 is a longitudinal cross sectional view (cut along the tracking grooves 170) of the mixing chamber 134 of the reflective disc 110 showing the inlet port 122. FIG. 23 includes the substrate 120, the reflective layer 142 and the active layer 144 applied over the reflective layer 142. As further illustrated in FIG. 23, the plastic adhesive member 118 is applied over the active layer 144. FIG. 23 also shows the cap portion 116 and the reflective surface 146 associated therewith. Thus when the cap is applied to the plastic adhesive member 118 including the desired cut-out shapes, the flow channel is thereby formed, including, in this embodiment, the mixing chamber 134.

Figure 24:
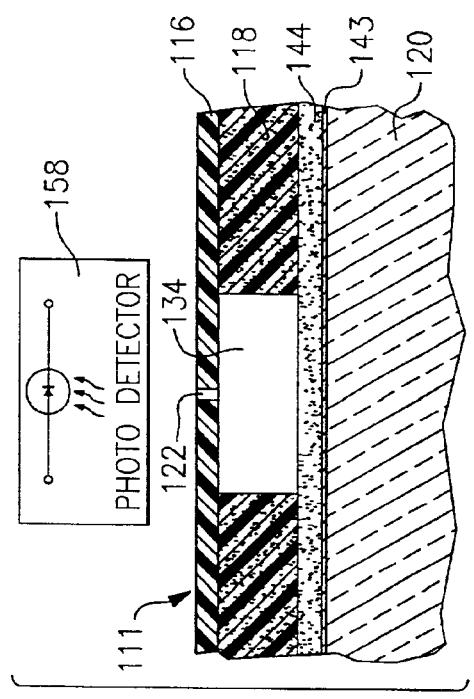
FIG. 24 is a longitudinal cross sectional view (cut along the tracking grooves) of the mixing chamber of the transmissive bio-disc showing the inlet port.

FIG. 24 is a longitudinal cross sectional view (cut along the tracking grooves 170) of the mixing chamber 134 of the transmissive disc 111 showing the inlet port 122. FIG. 24 is an alternate embodiment to the reflective disc 110 illustrated in FIG. 23, wherein a transmissive disc format is utilized as shown in FIG. 7. FIG. 24 illustrates the transmissive disc format with the clear cap portion 116 and the thin semi-reflective layer 143 on the substrate 120, as discussed in FIG. 7. FIG. 24 also shows the active layer 144 applied over the thin semi-reflective layer 143. The thin semi-reflective layer 143 may be made from a metal such as aluminum or gold which is approximately 100–300 Angstroms thick, allowing the incident or interrogation beam to penetrate and pass through the disc and thus be detected by the top detector 158.

Figure 25:
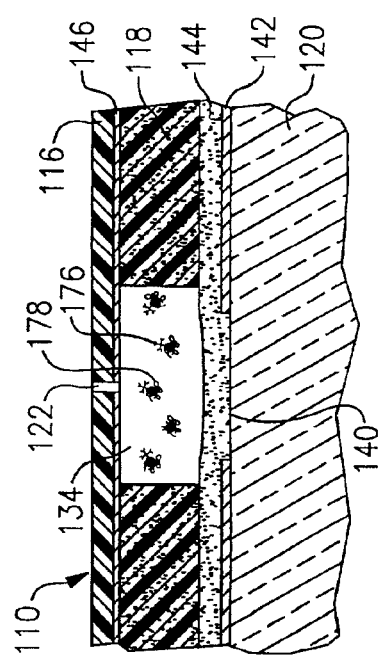
FIG. 25 is a longitudinal cross sectional view (cut along the tracking grooves) of a mixing chamber of a reflective bio-disc containing conjugated enzyme.

FIG. 25 is a longitudinal cross sectional view (cut along the tracking grooves 170) of a mixing chamber 134 of the reflective disc 110 showing an inlet port 122. Similar to FIG. 23, the principle elements of the reflective disc as described in FIG. 2A are also present. FIG. 25 further illustrates the enzymes 178, each conjugated with the binding agent 180, pre-loaded into the mixing chamber 134.

Figure 26:
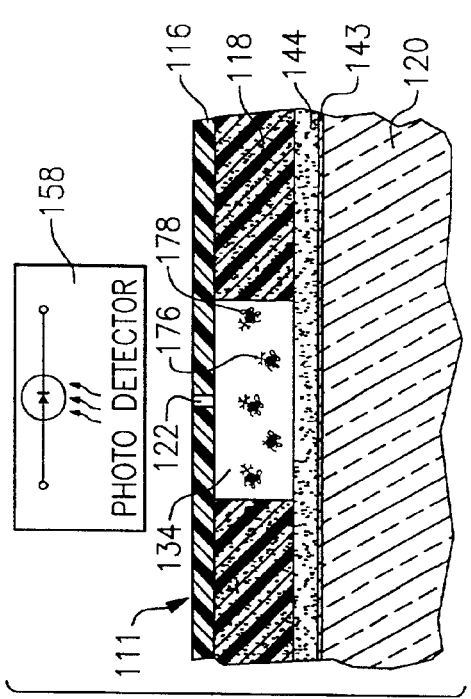
FIG. 26 is a longitudinal cross sectional view (cut along the tracking grooves) of a mixing chamber of a transmissive bio-disc containing conjugated enzyme.

FIG. 26 is a longitudinal cross sectional view (cut along the tracking grooves 170) of the mixing chamber 134 of the transmissive disc 111 showing the inlet port 122. Similar to FIG. 24, the principle elements of the reflective disc 110 as described in FIG. 3A are also present. In this alternative embodiment, the enzymes 178, each conjugated with the binding agent 180, are pre-loaded into the mixing chamber 134.

Figure 27:
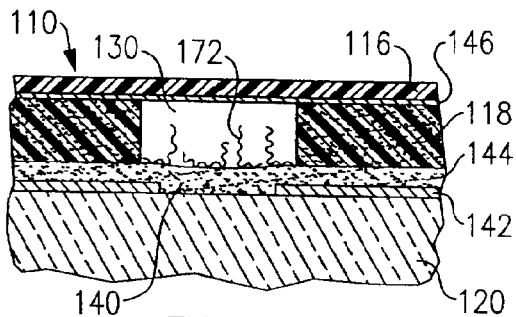
FIG. 27 is a longitudinal cross sectional view of a reflective bio-disc, similar to FIG. 6, which shows the capture DNA attached to the active layer within the target zone.
Figure 28:
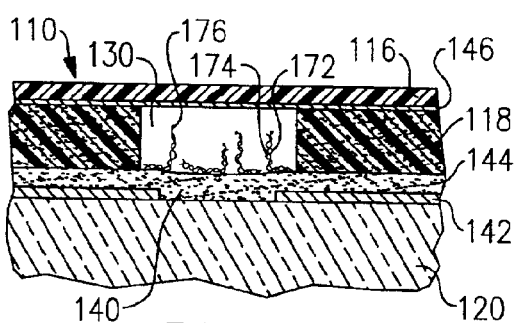
FIG. 28 is a longitudinal cross sectional view of a reflective bio-disc, similar to FIG. 6, which shows the flow channel and target zone after hybridization of the target DNA with the capture DNA.
Figure 29:
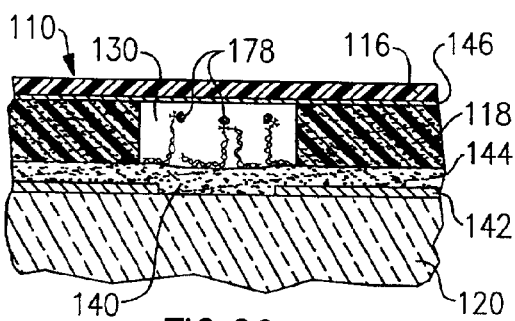
FIG. 29 is a longitudinal cross sectional view of a reflective bio-disc, similar to FIG. 6, which shows enzymes bound to the target DNA hybridized to the capture DNA.

Referring next to FIGS. 27–29, there are illustrated longitudinal cross sectional views of the reflective optical bio-disc 110, similar to FIG. 6, which contains all components for the reflective disc 110 as discussed for FIG. 6. FIG. 27 illustrates the capture DNA 172 attached to the active layer 144 within the target zone 140. In this embodiment, capture DNA 172 attaches to the active layer 144 by either passive adhesion or covalent bonding. Application of a small volume of capture DNA 172 solution to the active layer 144 forms clusters of capture DNA 172 within the area of the target zone 140, as illustrated.

FIG. 28 shows the flow channel 130 and target zone 140 after hybridization of the target DNA 174 with the capture DNA 172. In addition, FIG. 28 shows the affinity agent 176 on the target RNA or DNA 174 or, alternatively, on signal DNA, as employed in the present invention and discussed above in conjunction with FIGS. 19 and 20. In one embodiment of the present invention, the affinity agent 176 includes biotin or any equivalent affinity agent.

FIG. 29 shows enzymes 178 bound to the hybridized capture DNA/target DNA. These enzymes are conjugated with binding agent 180 that binds to an affinity agent 176, either directly on the target DNA or on signal DNA hybridized to the target RNA or DNA.

Figure 30:
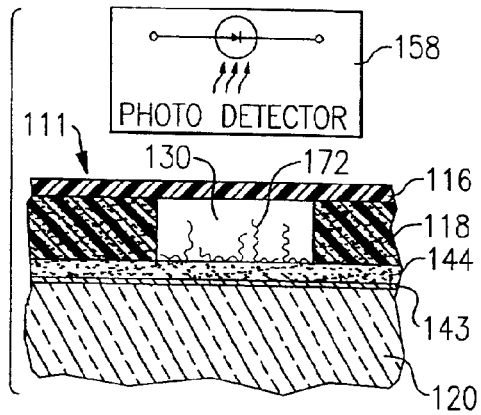
FIG. 30 is a longitudinal cross sectional view of a transmissive bio-disc, similar to FIG. 7, which shows the capture DNA attached to the active layer within the target zone.
Figure 31:
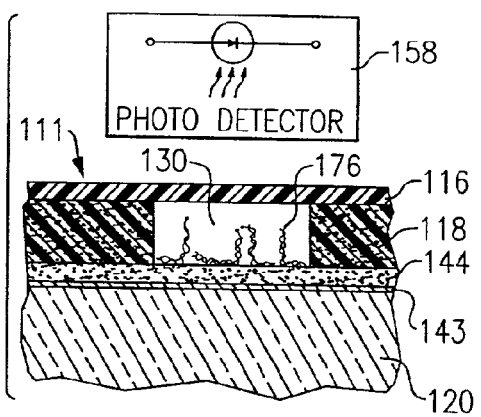
FIG. 31 is a longitudinal cross sectional view of a transmissive bio-disc, similar to FIG. 7, which shows the flow channel and target zone after hybridization of the target DNA with the capture DNA.
Figure 32:
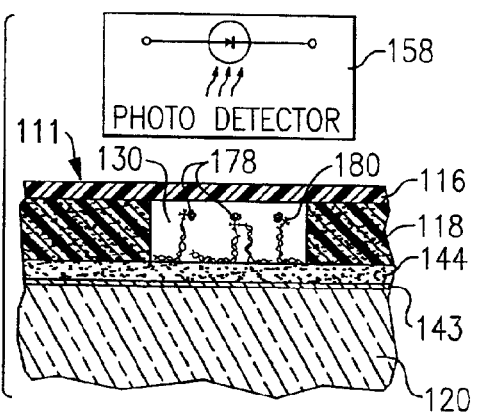
FIG. 32 is a longitudinal cross sectional view of a transmissive bio-disc, similar to FIG. 7, which shows enzymes bound to the target DNA hybridized to the capture DNA.

With reference now to FIGS. 30–32, there are shown yet another longitudinal cross sectional views of the transmissive optical bio-disc 111, similar to FIG. 7, which contains all components for the transmissive disc as discussed for FIG. 7. In this embodiment, the capture DNA 172 is attached to the active layer 144 within the target zone either by passive adhesion or covalent bonding. Application of a small volume of capture DNA 172 solution to the active layer 144 forms clusters of capture DNA 172 within the area of the target zone 140 as illustrated in FIG. 30.

FIG. 31 shows the flow channel 130 and target zone after hybridization of target RNA or DNA with the capture DNA. In addition, FIG. 31 shows the affinity agent 176 on the target RNA or DNA or, alternatively, on signal DNA. In one embodiment of the present invention, the affinity agent 176 includes biotin or any equivalent affinity agent.

FIG. 32 depicts the flow channel 130 and the target zone 140 after hybridization of target RNA or DNA with the capture DNA. In addition, FIG. 32 shows enzymes 178 as employed in the present invention. These enzymes 178 are conjugated with binding agent 180 that bind to the affinity agent 176 on the target DNA (or on the signal DNA hybridized to the target RNA or DNA).

Referring now to FIGS. 33A–33G, there is illustrated a method according to the present invention for detecting or determining the presence of target DNA 174 in a test sample in conjunction with the optical bio-disc according to the present invention. As shown in FIGS. 33A–33G and discussed above with reference to FIGS. 2 and 3, the optical bio-disc includes the cap portion 116, the adhesive member 118 and the substrate 120. The disc format may be either the reflective disc format 110 or the transmissive disc format 111 with varying elements to each respective cap portion 116 and substrate 120 as described above in conjunction with FIGS. 2 and 3.

Figure 33A:
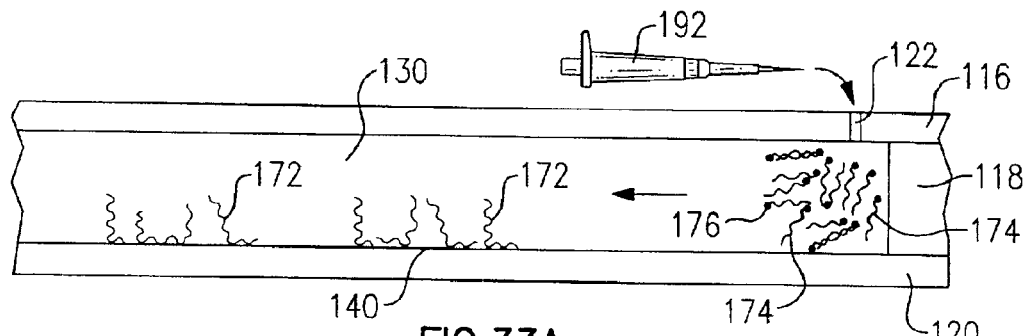
FIGS. 33A–33G show a longitudinal cross-section of a flow channel, illustrating a method according to the present invention for detecting or determining the presence of target DNA in conjunction with the optical bio-disc.
Figure 33B:
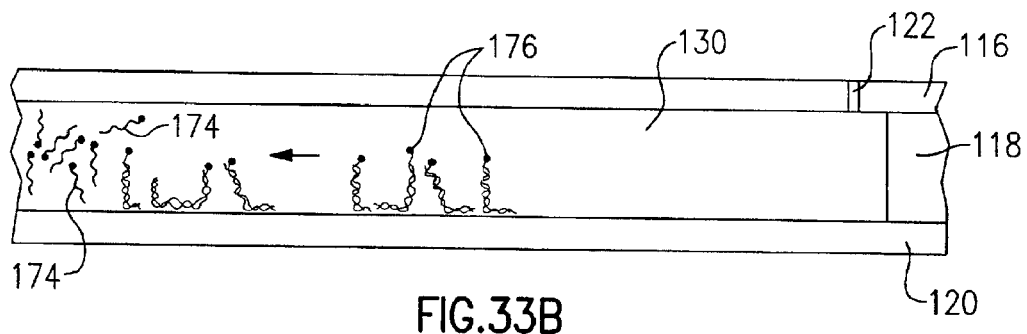

Although the disc composition between the different disc formats may vary, the biochemical interactions remain the same. In FIG. 33A, a pipette 192 is loaded with a test sample of DNA that has been linked to affinity agent 176. The test sample is injected or deposited into the flow channel 130 through the inlet or injection port 122. As the flow channel 130 is further filled with test sample, the target DNA 174 begin to flow or move down the flow channel 130 as illustrated in FIGS. 33A and 33B. When target DNA 174 of a specific sequence is present in the test sample, the target DNA 174 hybridizes with the capture DNA 172 as shown in FIG. 33B. In this manner, the target DNA 174 with its affinity agent 176 is retained within the target zone. Hybridization may be further facilitated by adjusting the temperature of the disc or the flow channel and/or ionic strength of the hybridization buffer to optimize annealing of the nucleic acids.

Figure 33C:
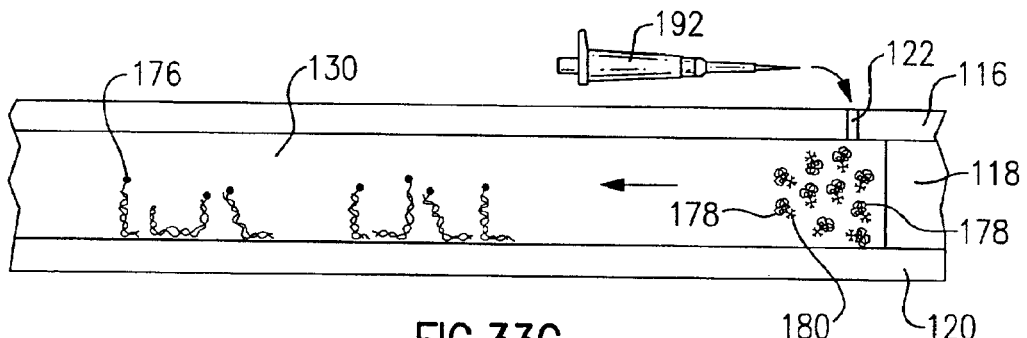

After hybridization, the flow channel 130 may be washed to clear the target zone 140 of any unattached DNA in the sample. After removing the unattached DNA in the sample, enzymes 178 with binding agent 180 are introduced in the channel, as shown in FIG. 33C. In one embodiment, enzymes are introduced via the input port 122, as shown in FIG. 33C. In an alternative embodiment, enzyme buffer is introduced through an enzyme buffer port into a side chamber (not shown), which is in fluid communication with the flow channel and which contains a pad or membrane onto which enzyme has been dried as described above in conjunction with FIG. 4. The buffer solubilizes the enzyme, which then flows into the flow channel 130.

Figure 33D:
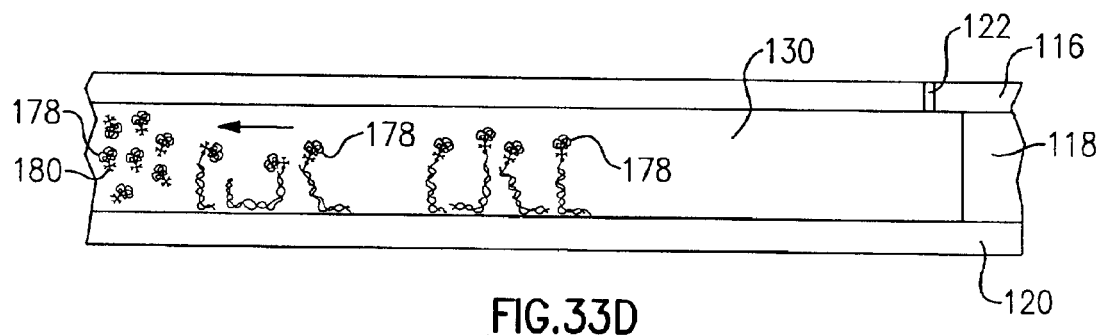

As the flow channel 130 is filled with enzyme solution, the enzymes 178 begin to flow or move down the flow channel 130 as illustrated in FIGS. 33C and 33D. When the enzyme comes into close proximity with the target DNA 174 hybridized in the target zone 140 with the capture probe, the enzymes 178 bind to the target DNA 174 via the interaction between the affinity agent 176 and the binding agent 180, as illustrated in FIG. 33D.

Figure 33E:
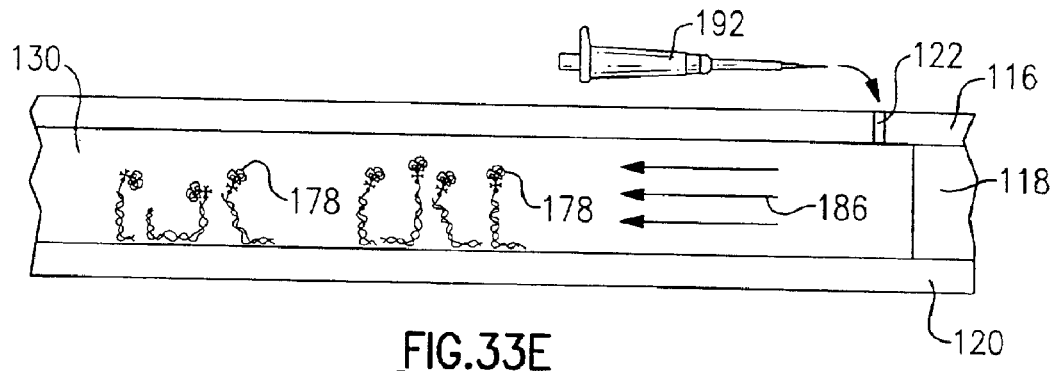

After enzymes 178 bind to the affinity agent 176, the flow channel 130 may be washed to clear the target zone 140 of any unattached enzyme 178. As shown in FIG. 33E, upon removal of unattached enzyme 178 in the solution, enzyme-reactive substrates 186 are then introduced in the channel as previously described with reference to FIG. 21. As the flow channel 130 is filled with enzyme substrate 186, the enzyme substrate 186 begin to flow or move down the flow channel 130 as illustrated in FIG. 33E. When the substrate comes in contact with the enzyme on the target DNA, the enzyme substrate reaction 194 occurs, which results in the production of a signal agent as described with reference to FIGS. 22A–22D. The signal agent may be color production or luminophore production, or it may be insoluble precipitate 190 formation as illustrated in FIG. 33G and FIGS. 22A to 22D.

Figure 33F:
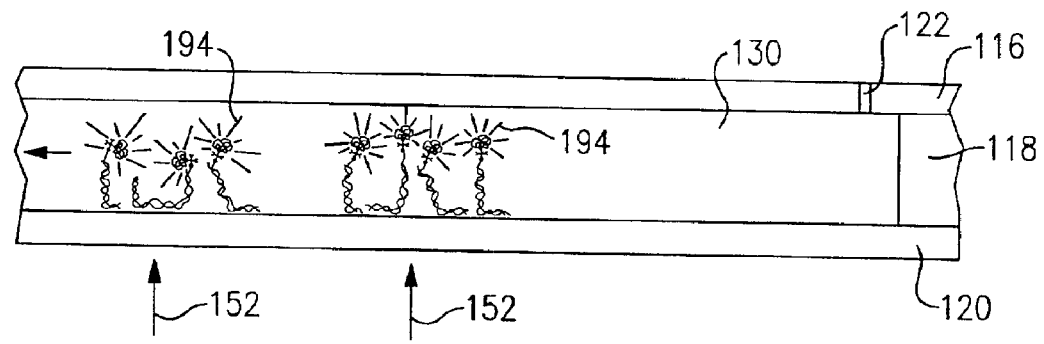
Figure 33G:
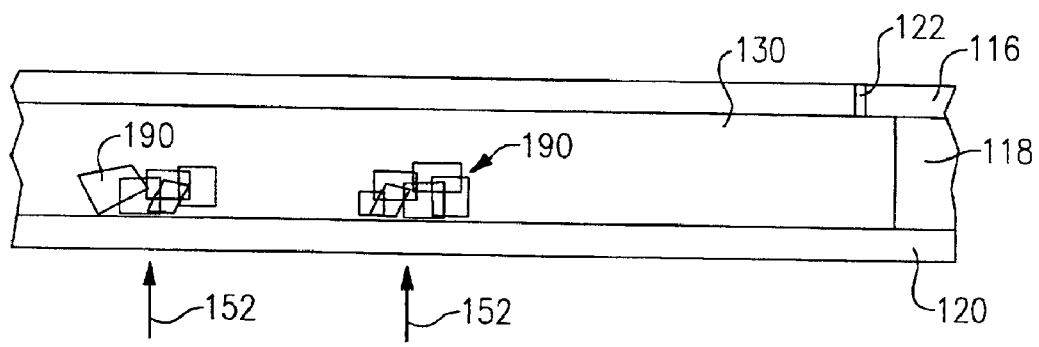

The interrogation beam 152 may then be scanned through the target zone 140 to determine the presence of signal agents as illustrated in FIGS. 33F and 33G. In the event no target DNA 174 is present in the test sample, no enzyme substrate reaction 194 will occur and the signal agents will not be present. In this case, when the interrogation beam 152 is directed into the target zone 140, a negative or baseline reading will result, thereby indicating that no target DNA 174 was present in the sample.

Referring next to FIGS. 34A–34H, there is illustrated another method according to the present invention for detecting or determining the presence of target RNA or DNA 174, in a sample of DNA or RNA, in conjunction with the optical bio-disc 110 or 111 according to the present invention. As shown in FIGS. 34A–34H and discussed in FIGS. 2 and 3, the optical bio-disc 110 or 111 includes the cap portion 116, the adhesive member 118 and the substrate 120. The disc format may be either the reflective disc format 110 or the transmissive disc format 111 with varying elements to each respective cap portion 116 and substrate 120 as described in FIGS. 2 and 3. Although the disc composition of different disc formats may vary, the biochemical interactions remain the same.

Figure 34A:
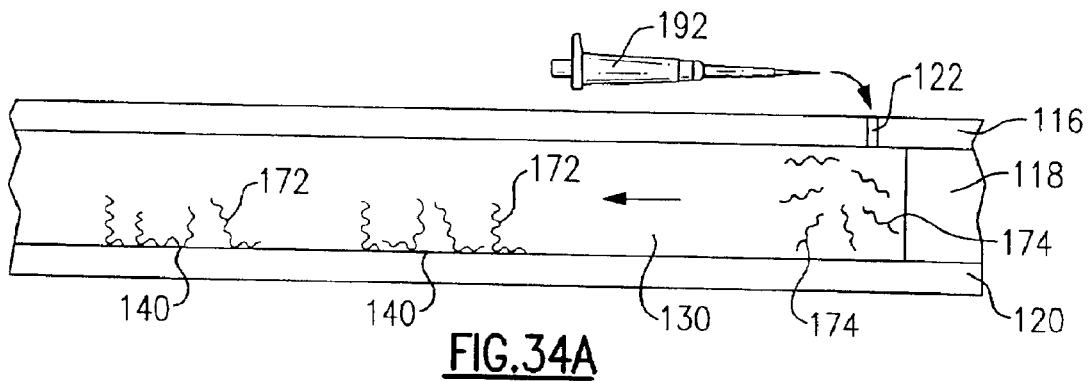
FIGS. 34A–34H show a longitudinal cross-section of a flow channel, illustrating another method according to the present invention for detecting or determining the presence of target DNA in conjunction with the optical bio-disc, utilizing signal DNA.
Figure 34B:
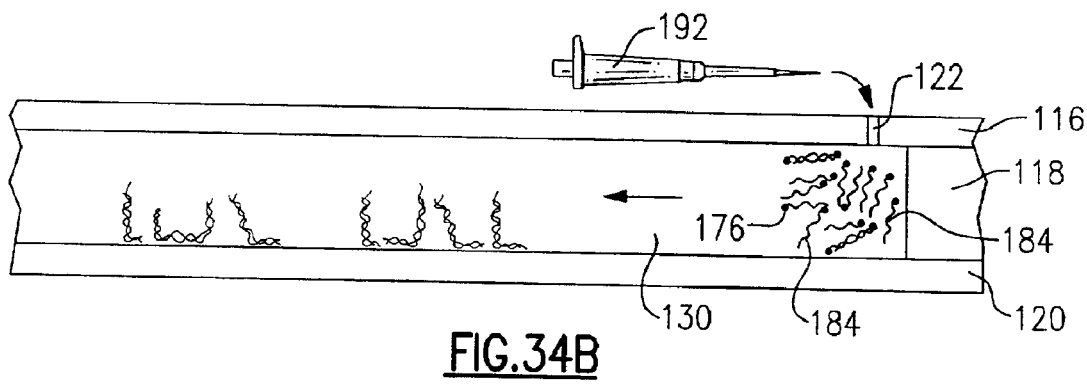

In FIG. 34A, the pipette 192 is loaded with a test sample of DNA or RNA. The test sample is injected or deposited into the flow channel 130 through inlet or injection port 122. As the flow channel 130 is further filled with test sample, the target RNA or DNA 174 begin to flow or move down the flow channel 130 as illustrated in FIG. 34A. When target RNA or DNA 174 of a specific sequence is present in the test sample, the target RNA or DNA 174 hybridizes with the capture DNA 172, as shown in FIG. 34B. Hybridization may be further facilitated by adjusting the temperature of the disc and/or the flow channel and/or adjusting the ionic strength of the hybridization buffer to optimize annealing of the nucleic acids. The techniques for optimizing oligonucleotide hybridization is well know in the art.

Figure 34C:
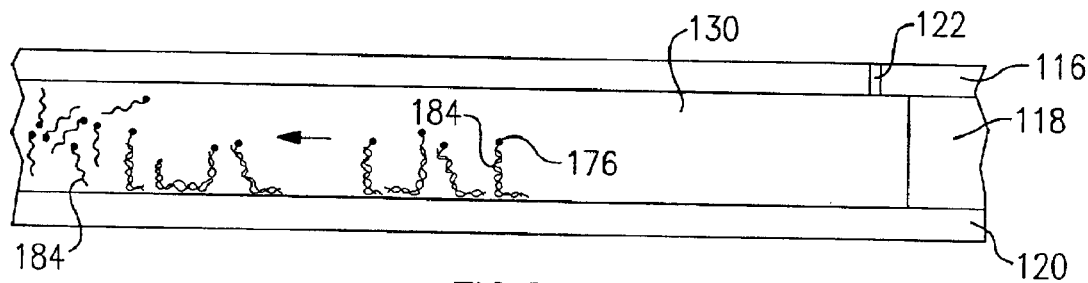

After hybridization, the disc may be washed to clear the target zone 140 of any unattached DNA or RNA sample. Upon removing the unattached DNA or RNA in the sample, signal DNA probes 184 containing an affinity agent 176 are introduced into the flow channel 130, as shown in FIG. 34B. As the flow channel 130 is further filled with signal DNA 184, the signal DNA begins to flow or move down the flow channel 130 as illustrated in FIGS. 34B and 34C. When signal DNA 184 comes in contact with the target RNA or DNA 174, which is hybridized with the capture DNA 172 in the target zone 140, the signal DNA 184 hybridizes with the target RNA or DNA 174 and is retained in the target zone as shown 34C and above in FIG. 20. In this manner, the target RNA or DNA 174 and signal DNA 184 probe with its affinity agent 176 are retained within the target zone 140. Hybridization may be further facilitated by adjusting the temperature of the disc and/or the flow channel to optimize annealing of the nucleic acids.

Figure 34D:
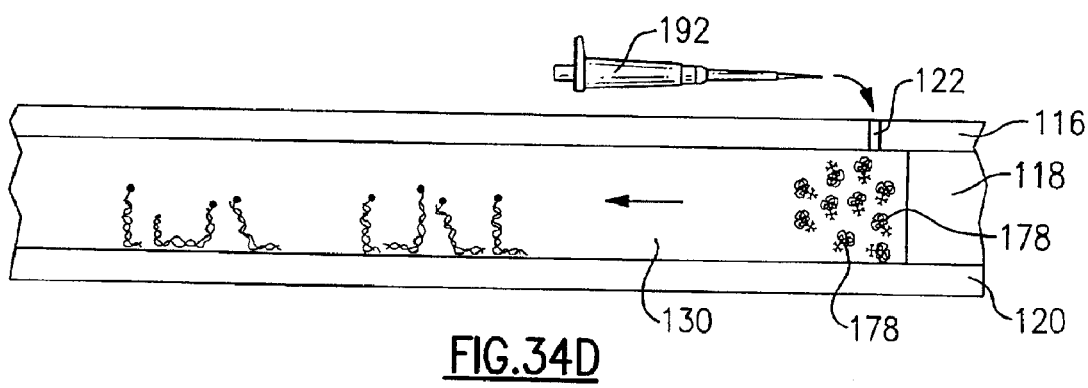
Figure 34E:
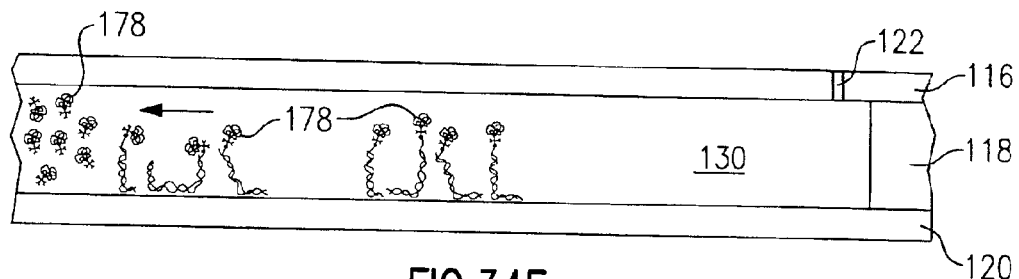

After hybridization, the flow channel 130 may be washed to clear the target zone 140 of any unattached signal DNA 184 probes. As shown in FIG. 34D, after the removal of the unattached signal DNA 184 probes in the sample, enzymes 178 are introduced in the channel. In one embodiment, enzymes are introduced via the input port 122, as shown in FIG. 34D. In an alternative embodiment, enzyme buffer is introduced through an enzyme buffer port into a side chamber (not shown), which is in fluid communication with the flow channel and which contains a pad or membrane onto which enzyme has been dried as discussed above in conjunction with FIG. 4. The buffer solubilizes the enzyme, which then flows into the flow channel.

As the flow channel 130 is filled with enzyme solution, the enzymes 178 begin to flow or move down the flow channel 130 as illustrated in FIG. 34D. When the enzyme 178 comes into close proximity with the hybridized signal DNA/target DNA/capture DNA complex in the target zone 140, the enzymes 178 bind to the signal DNA 184 via the interaction between the affinity agent 176 and binding agent 180, best shown in FIG. 20 and as further illustrated in FIG. 34E.

Figure 34F:
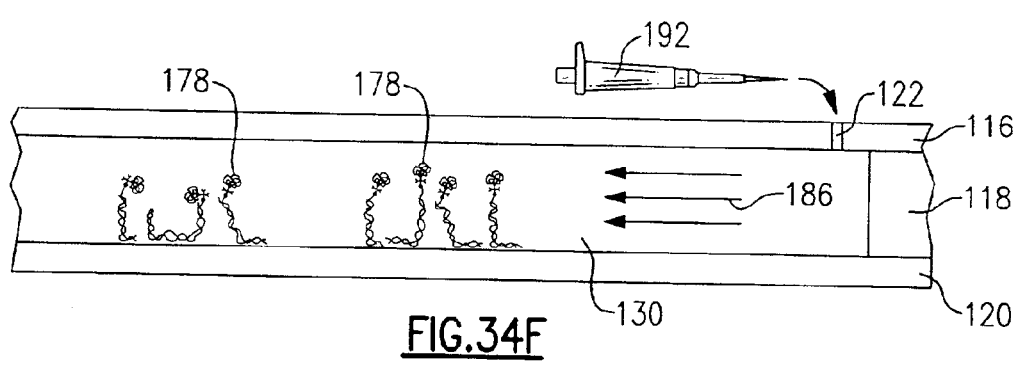
Figure 34G:
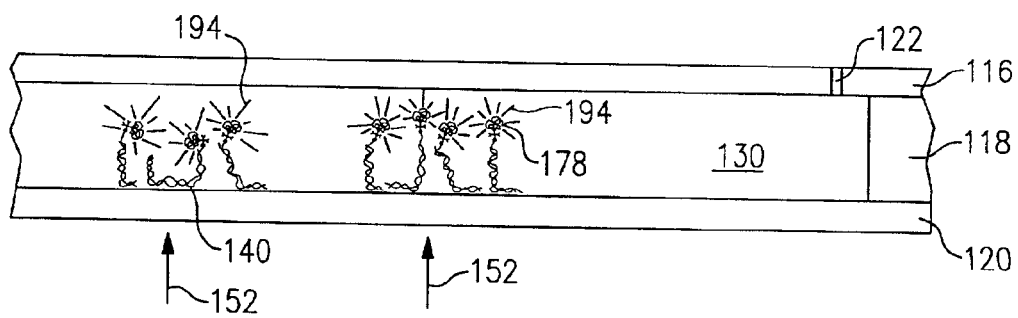

After enzyme binding, the flow channel 130 may be washed to clear the target zone 140 of any unattached enzyme 178. After removing unbound enzymes 178, the enzyme substrate 186 is introduced in the channel, as illustrated in FIG. 34F. As the flow channel 130 is filled with enzyme substrate 186, the enzyme substrate 186 begin to flow or move down the flow channel 130. When the enzyme substrate 186 comes in contact with the enzyme 178 bound to the target zone 140 via the signal DNA/target DNA/capture DNA complex, the enzyme substrate reaction 194 occurs, which results in the production of a signal agent, as shown in FIG. 34G. The signal agent may be a color production, luminophore production, fluorescence, or the formation of insoluble precipitate 190 as illustrated in FIG. 34H and FIGS. 22A to 22D.

Figure 34H:
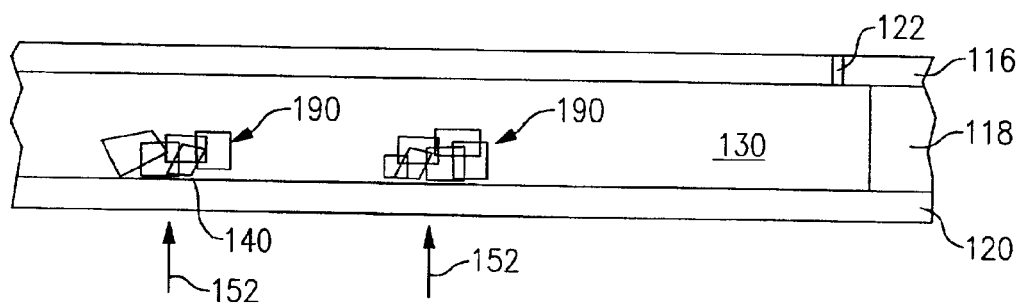

The interrogation beam 152 is then scanned through the target zone 140 to determine the presence of signal agents, as illustrated in FIGS. 34G and 34H. If no target DNA 174 is present in the test sample, no enzyme substrate reaction 194 will occur and the signal agents will not be present. In this case, when the interrogation beam 152 is directed into the target zone 140, a negative or baseline reading will result, thereby indicating that no target DNA was present in the sample.

With reference now to FIGS. 35A–35F, there is illustrated yet another method according to the present invention for detecting or determining the presence of target RNA or DNA 174 in a test sample in conjunction with the optical bio-disc according to the present invention. As shown in FIGS. 35A–35F and discussed with reference to FIGS. 2 and 3, the optical bio-disc includes the cap portion 116, the adhesive member 118 and substrate 120. The disc format may be either the reflective disc format 110 or the transmissive disc format 111 with varying elements to each respective cap portion 116 and substrate 120 as described in FIGS. 2 and 3. The target RNA or DNA 174 may be detected using either disc format. Although the disc composition of different disc formats may vary, the biochemical interactions remain the same.

Figure 35A:
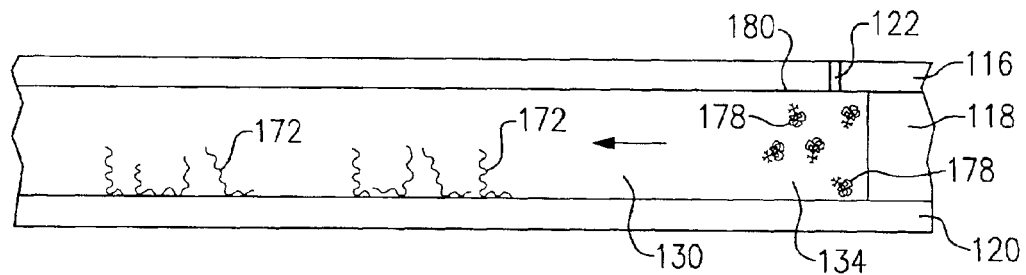
FIGS. 35A–35F show a longitudinal cross-section of a flow channel, illustrating yet another method according to the present invention for detecting or determining the presence of target DNA in conjunction with the optical bio-disc, in which enzymes with the associated binding agent are pre-loaded in a mixing chamber.
Figure 35B:
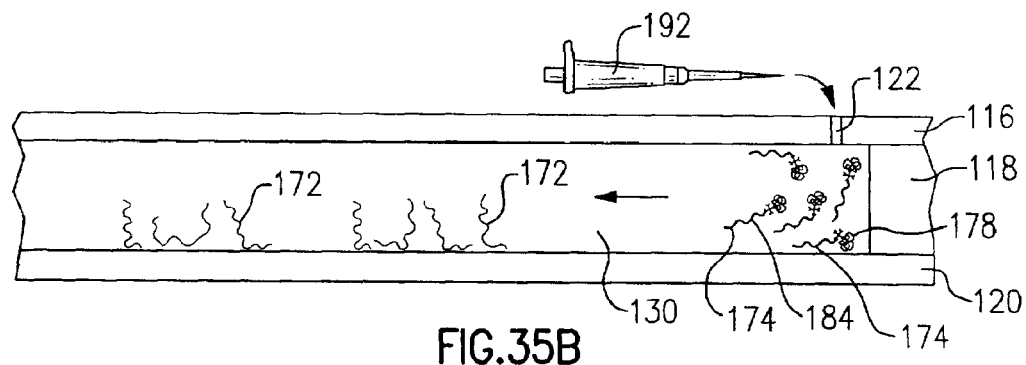

In FIG. 35A, enzymes 178 with the associated binding agent 180 are pre-loaded in a mixing chamber 134. In FIG. 35B, the pipette 192 is loaded with a test sample solution containing DNA that has been linked to affinity agent 176 or, alternatively, a test sample solution of DNA or RNA that has been pre-hybridized with a signal DNA probe 184 containing an affinity agent. The test sample solution is injected or deposited into the flow channel 130 through inlet or injection port 122.

As the flow channel 130 is further filled with test sample solution, the target RNA or DNA 174, the signal DNA 184 probe (if present), and the enzymes 178 begin to flow or move down the flow channel 130 as illustrated in FIG. 35B. FIG. 35B also shows the binding of the pre-loaded enzymes 178 with the target DNA 174 or, if present, with the signal DNA/target DNA complex, through the interaction of the affinity agent and binding agent.

Figure 35C:
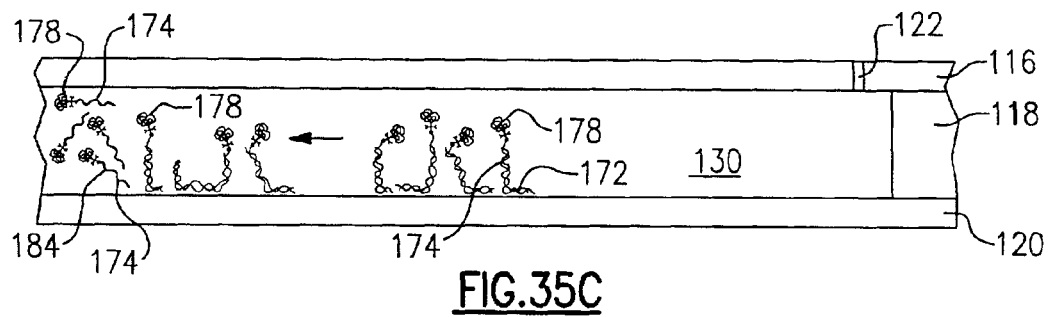

When target RNA or DNA 174 of a specific sequence is present in the test sample, the target RNA or DNA 174 hybridizes with the capture DNA 172 as shown in FIG. 35C. In this manner, the enzymes 178, attached to the target DNA 174 as described in FIG. 18 (or to the target RNA or DNA/signal DNA complex as described in FIGS. 19 and 20), are retained within the target zone 140. Hybridization may be further facilitated by heating the disc or a local area thereof.

Figure 35D:
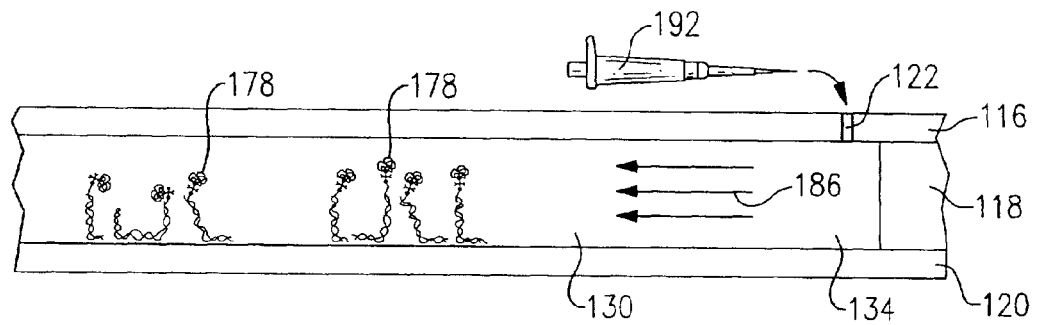
Figure 35E:
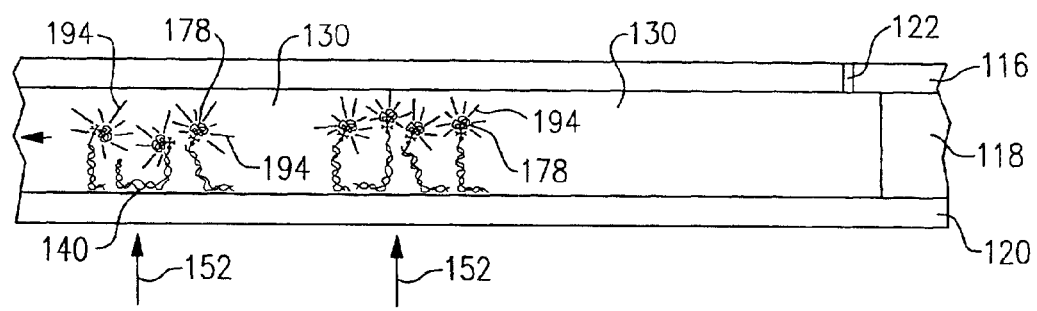

After hybridization, the flow channel 130 may be washed to clear the target zone 140 of any unattached target RNA or DNA, after which enzyme substrate 186 is introduced into the channel, as shown in FIG. 35D. As the flow channel 130 is filled with enzyme substrate 186, the enzyme substrate 186 begin to flow or move down the flow channel 130. When the substrate comes in contact with the enzyme 178, the enzyme substrate reaction 194 occurs, producing a signal agent, as shown in FIG. 35E. The signal agent may be color production or luminophore production. The signal agent may also be the formation of a precipitate 190, as illustrated in FIG. 35F and above in FIGS. 22A–22D.

Figure 35F:
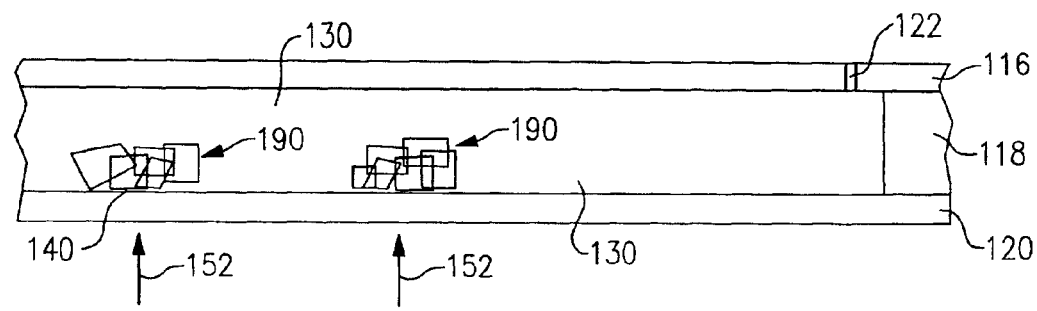

The interrogation beam 152 is scanned through the target zone 140 to determine the presence of signal agents, as illustrated in FIGS. 35E and 35F. In the event no target DNA 174 is present in the test sample, no enzyme substrate reaction 194 will occur and the signal agents will not be present. In this case, when the interrogation beam 152 is directed into the target zone 140, a negative or baseline reading will result thereby indicating that no target DNA 174 was present in the sample.

Data Generated from the Assay

Figure 36:
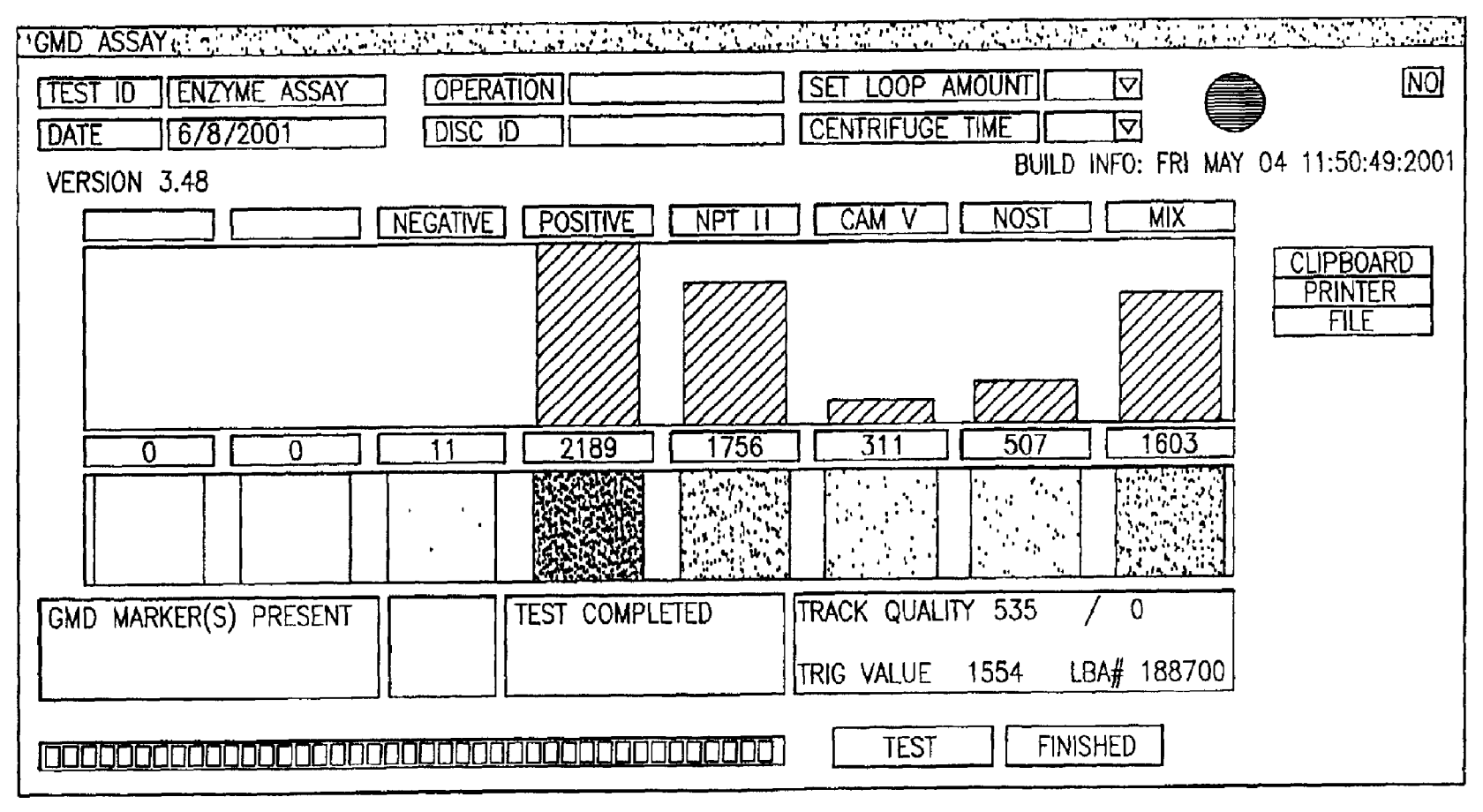

FIG. 36 is an example of a data output collected using an optical disc reader and its respective software. The output data illustrated in FIG. 36 was collected using a reflective disc format (FIGS. 2 and 6) with 8 target zones 140 and an event counting software. The event counting software used for reaction product detection in the optical disc reader is disclosed in the above referenced commonly assigned U.S.

Provisional Application No. 60/291,233. In this embodiment, the first two target zones were not used in this experiment (counting from left to right). Target zone 3 was a blank (no capture probe) negative control. Target zone 4 contained a single strand DNA bound to the active layer 144 with an affinity agent 176 attached, which served as the positive control. Target zones 5, 6 and 7 contained capture DNA 172 attached to the active layer 144, which was selected to be complementary to various target DNA sequences: NPTII, CamV, and NosT, respectively. Target zone 8 contained a mixture of all the three capture DNA 172 probes, NPTII, CamV, and NosT, attached to the active layer 144. Accordingly, target zone 8 will bind any or all of the three target DNA molecules. In this test, NPTII showed the highest signal, followed by NosT then CamV. The sample used in this test were amplicons from a multiplex PCR amplification. Further details relating to other aspects associated with data acquisition, processing, collecting, and reporting are disclosed in, for example, commonly assigned co-pending U.S. Provisional Patent Application Ser. No. 60/291,233 entitled "Variable Sampling Control For Rendering Pixelation of Analysis Results In Optical Bio-Disc Assembly And Apparatus Relating Thereto" filed May 16, 2001, U.S. Provisional Patent Application Ser. No. 60/348,767 entitled "Optical Disc Analysis System Including Related Signal Processing Methods and Software" filed Jan. 14, 2002, and U.S. Provisional Patent Application Ser. No. 60/352,625 entitled "Logical Triggering Methods and Apparatus for Use with Optical Analysis Discs and Related Disc Drive Systems" filed Jan. 28, 2002, all of which are incorporated herein by reference in their entirety.

Figure 37:
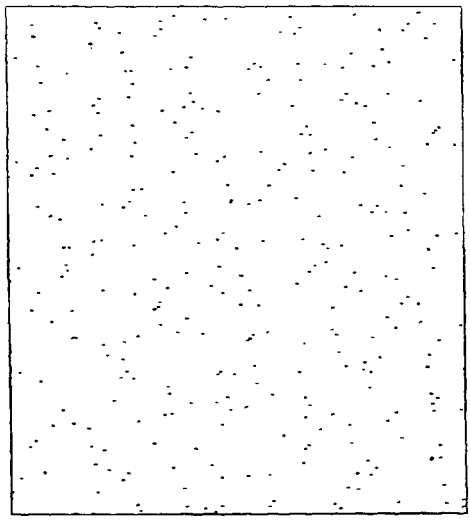
FIG. 37 is a series of pictorial representations illustrating image detection according to one embodiment of the present invention.
Figure 37:
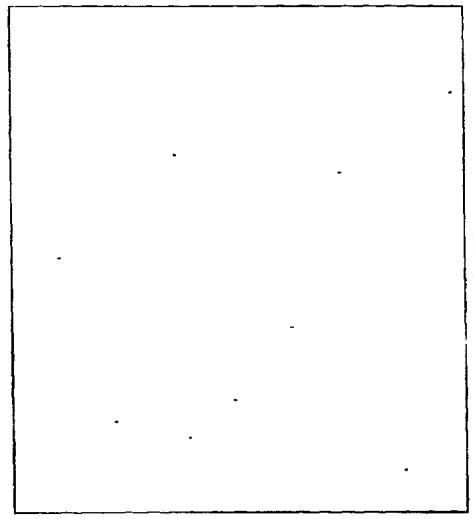
Figure 37:
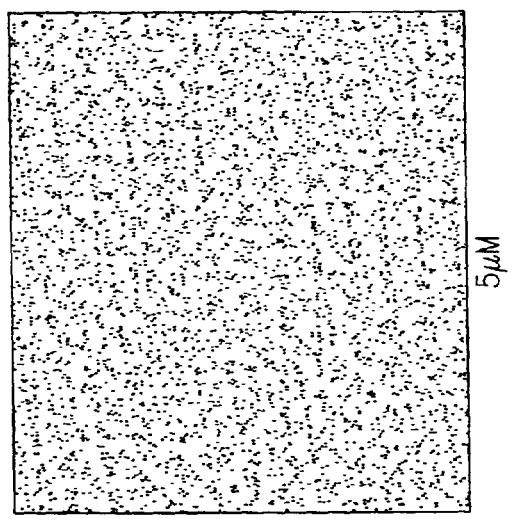
Figure 37:
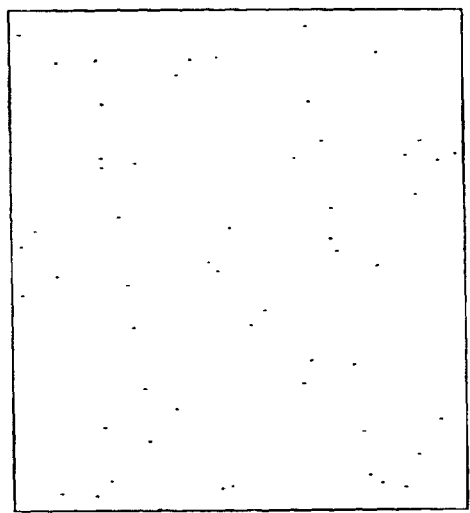

Referring to FIG. 37, there is shown a series of pictorial representations illustrating image detection according to one embodiment of the present invention. These results demonstrate microscopic micrographs of pellets/precipitate on the active layer of the transmissive disc format as described above in conjunction with FIG. 22D. Various concentrations (0 to 5 uM) of single stranded DNA containing an affinity agent 176 were deposited onto the active layer 144. Enzymes 178 with binding agent 180 were then allowed to bind to the DNA on the active layer 144 via affinity-binding agent interaction. The solution of enzyme substrate 186 was then introduced and pellet formation was observed in a concentration dependent manner.

The test results of any of the test methods described above may be readily displayed on the display monitor 114 shown in FIG. 1. The optical bio-disc 110 or 111 according to the present invention may include encoded software that interacts with the drive, the controller 164, the processor 166, and the analyzer 168 as shown in FIGS. 1 and 5. The interactive software is implemented to facilitate the methods described herein and display the results. In the preferred embodiment, the software is used to quantify signal differentiation based upon luminescence, color changes, and/or pellet/precipitate formation.

Applications of the Present Invention

As will be appreciated, the enzyme-based assay for detecting and analyzing nucleic acids in test samples has a number of potential applications. For example, this assay can be used to test for the presence of specific disease causing agents, such as viruses or bacteria, in biological samples taken from patients. Capture DNA probes specific for various disease causing organisms can be deposited in specified target zones on a bio-disc in an ordered array (or microarray). Multiplexed PCR reactions, using mixed primer sets directed to these various disease causing organisms, can be conducted on patient samples, and the resulting amplicons used as target DNA probes in the bio-disc assay system. Enzyme reactions can be monitored as described above to determine which target zones in the ordered array produce a detectable signal. These target zones can then be correlated to the specific capture DNA probe deposited at that location, allowing clinicians to quickly identify which target DNA molecules are amplified from the patient sample and, accordingly, which disease causing organism is likely present in the patient.

Similarly, the present invention can be used to test water and soil samples for specific microorganisms and is also helpful in monitoring agricultural products as, for example, in testing for the presence of genetically modified organisms (GMO). For example, crop samples can be amplified using primer sets specific for a marker gene in a genetically modified plant and for intrinsic plant genes, such as lectin or zein. The amplified target DNA can then be used on biodiscs containing capture probes for both the marker gene and for intrinsic plant genes. Calibration controls can also be run simultaneously, in which known concentrations of the GMO are amplified for use as target DNA. By comparing the reaction products of the unknown sample with the calibration curve, the presence of genetically modified organisms in a sample can be detected and quantified.

Figure 38:
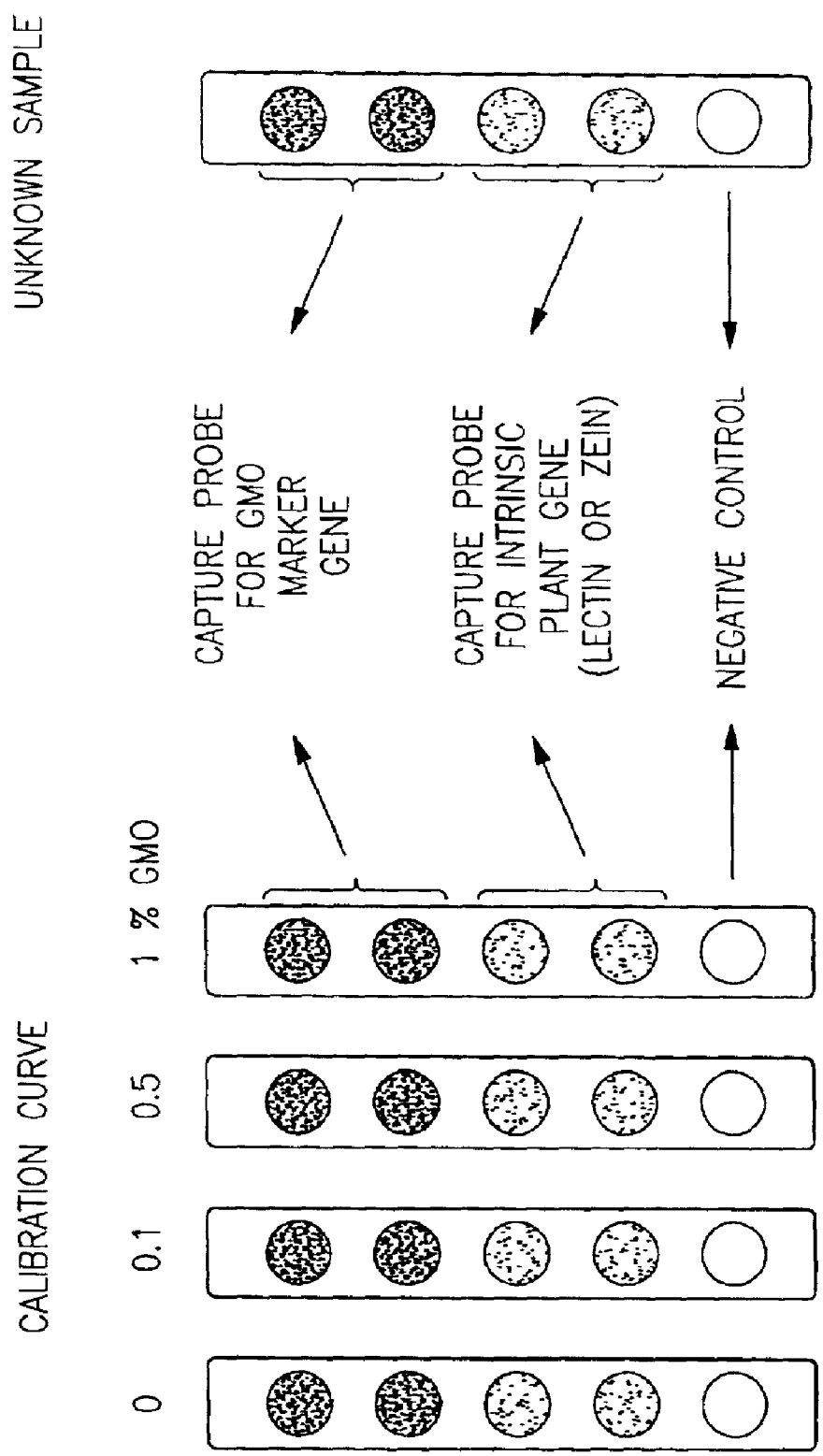
FIG. 38 is a schematic overview of one embodiment of the present invention useful in detecting and quantifying genetically modified material.

An overview of how the present invention can be used in detecting and quantifying GMOs is shown in FIG. 38. A crop product, for example, corn, is suspected of containing some portion of genetically modified corn. A marker gene is identified that is specific for the genetically modified corn, and capture probes are synthesized that are specific for that marker gene. Intrinsic plant gene probes, such as those specific for the gene lectin, are also synthesized.

An optical bio-disc containing at least five flow channels is prepared with five target zones in each flow channel (as will be appreciated, these numbers may be varied depending on the particular assay): two for the marker gene capture probe, two for the lectin capture probe (as positive controls), and one with a non-specific probe, as a negative control. Each of these flow channels is depicted in FIG. 38. Five separate PCR reactions are performed to produce target DNA using primer sets directed to both the marker gene and the lectin gene. Four of the reactions are performed using template DNA from calibration standards containing known quantities of GMO (e.g., 0%, 0.1%, 0.5% or 1% GMO); the fifth reaction is performed using the unknown sample. Each set of DNA sample is hybridized to one of the flow channels and the enzyme reaction is performed as described herein. The detectable signal, as, for example, measured by the amount of an insoluble precipitate or pellet formation, for the unknown sample is compared to those of the calibration curve, allowing the presence (and amount) of GMO in the unknown sample to be determined. If the signal in the unknown sample is too high to permit quantification, it may be necessary to repeat the procedure with dilutions of the unknown sample.

Optical Bio-discs with Egui-radial Fluidic Circuits

The optical bio-disc systems and methods for detecting specific sequences of oligonucleotides, as described above, may be readily implemented in an optical bio-disc with an equi-radial fluidic circuit. Details regarding optical bio-dics with equi-radial fluidic circuits is disclosed in, for example, commonly assigned co-pending U.S. Provisional Patent Application Ser. No. 60/353,014 entitled "Optical Discs Including Equi-Radial and/or Spiral Analysis Zones and Related Disc Drive Systems and Methods" filed Jan. 29, 2002, which is incorporated herein by reference in its entirety.

Experimental Examples

Having generally described the invention, the same will be more readily understood through reference to the following examples, which are provided by way of illustration, and are not intended to be limiting of the present invention.

Example 1

Spin Coating the Bio-disc

Fresh polystyrene solution was prepared by adding 3 g polystyrene pellets (Sigma cat. no. 182427; molecular weight=280,000) to 310 ml toluene and stirring for 1 hour using a teflon stir bar and a stir plate. After the polystyrene was completely dissolved in the toluene, 68 ml reagent grade isopropanol was slowly added while stirring.

A stock solution of nitrocellulose was prepared by diluting a nitrocellulose collodium solution (4–8% in ethanol/diethylether, Fluka cat. no. 09986, lot no. 389973/1 30299) 1:5 in reagent grade ethanol. Prior to spin coating, the stock solution was diluted 1:10 with reagent grade ethanol and filtered using a 0.2 µm syringe filter.

A polycarbonate disc having a 200 Angstrom gold semi-reflective layer (BTI Optical Bio-disk Set FDL21:E001308) was placed on a "spin coater," or modified centrifuge, with the reflective surface up. While rotating the disc on the spin coater, the reflective surface was cleaned with reagent grade alcohol.

The spin coater was set to start spinning at 2500 rpm, followed by acceleration to 4000 rpm within 10 seconds. During this 10-sec acceleration, a steady stream of polystyrene solution was applied to the disc using a pasteur pipette, with the polystyrene solution applied from the outer edge to the inner side in one smooth stroke.

The spin coater speed was then adjusted to 1500 rpm, and the diluted and filtered nitrocellulose solution was applied onto the inner portion of the disc in a steady stream using a pasteur pipette.

Example 2

Preparing the Bio-disk for the Enzyme Assay

The disc from Example 1 was placed on a CD assembler/spindle with the nitrocellulose layer up. Between about 0.5 to 2.0 µl of 1 µM oligo probes (capture DNA) in 1 M $NH_4OAc$ were applied to the disk at defined target zones. The droplets of capture DNA were dried onto the nitrocellulose at 37° C.

A cover disc containing U-shaped fluidic circuits (50 µM adhesive; Fraylock, DBL243a) was applied using a disk assembler spindle, and the disc was run through a wringer to seal the two disks.

Example 3

General Enzyme DNA Assay

DNA blocking solution (1% bovine serum albumin [BSA], 5× Denhardt's solution, 0.1 mg/ml salmon sperm DNA, 200 mM KCl, 10 mM $MgCl_2$, 50 mM Tris, pH 7.4) was degassed in a vacuum desiccator and injected into the fluidic circuits of a bio-disc prepared as in Example 2, taking care that no air bubbles remained in the circuits. The bio-disc was then incubated at room temperature for 30 to 60 minutes.

The DNA blocking solution was removed, and the fluidic circuits washed with hybridization buffer (200 mM NaCl, 10 mM $MgCl_2$, 50 mM Tris, pH 7.4) injected into the fluidic circuits using a syringe. PCR amplicons (target DNA amplified using biotinylated primer sets, purified using the Qiagen QIAquick PCR Purification Kit, cat. no. 28104, lot no. 10927932, and eluted using hybridization buffer) were denatured at 95° C. for 5 minutes and immediately placed on ice for 5 minutes.

The denatured amplicons were added to the appropriate fluidic circuits (10 µl per fluidic circuit) and allowed to hybridize for 1.5 to 2 hours at room temperature. Following hybridization, the fluidic circuits were washed with hybridization buffer using a syringe.

Neutravidin-Horseradish Peroxidase Conjugated enzyme (N-HRP; Pierce product no. 31001, lot no. BK46404) was diluted 1:5000 in hybridization buffer, and 12 µl was applied to each fluidic circuit. The disc was then incubated at room temperature for 15 minutes.

The fluidic circuits were then washed with hybridization buffer using a syringe, and 12 µl of TMB Substrate in Stable hydrogen peroxide buffer (Calbiochem cat. no. 613548, lot B34202) was added to each fluidic circuit. The enzyme reaction was allowed to proceed for 5 mintues, after which the reaction was stopped by flushing the fluidic circuits with distilled water using a syringe.

Each fluidic circuit was sealed with tape, and the bio-disc was then placed in a disc-reader, similar to that shown in FIG. 5, and scanned with a 780 nm lightbeam, with the light transmitted through the bio-disc at each target zone measured to detect changes in the amplitude of the transmitted light.

Example 4

Enzyme DNA Assay Used to Identify *Brucella* Strains

A bio-disc with 6 target zones was prepared as in Example 2, with 1.6 µl of 10 µM DNA oligonucleotides specific to one of the *Brucella* strains applied to three of the target zones, as indicated in Table 2, below. One target zone contained a mix of all three *Brucella* species, one target zone contained biotinylated DNA (positive control), and one target zone contained no capture DNA (background).

*Brucella* sp. genomic DNA was subjected to PCR amplification using forward/reverse primer sets directed to *B. melitensis* to generate target *B. melitensis* amplicons. Each reaction contained 1 ng/μl *Brucella* DNA, 0.2 μM biotinylated forward and reverse primers, 0.2 mM dNTPs, 0.05 U/μl Taq polymerase, 3.0 mM $MgCl_2$ and 1× PCR buffer (Qiagen; 15 mM $MgCl_2$). The thermocycle conditions were:

| | |
|---|---|
| Step 1: | 95° C. for 12.5 minutes |
| Step 2: | 95° C. for 0.5 minute |
| Step 3: | 57° C. for 0.5 minute |
| Step 4: | 72° C. for 0.5 minute |
| Step 5: | Repeat Steps 2–4 34 times |
| Step 6: | 72° C. for 5.0 minutes |

The enzyme DNA assay was performed as described in Example 3, both without the addition of the target *B. melitensis* amplicons (results indicated in Table 2) and with the addition of purified target *B. melitensis* amplicons (results indicated in Table 3). Values from Tables 2 and 3 are event counts collected using an optical disc reader using the reflective disc format. The counting area was a rectangle, 940 μm×2300 μm; event count amplitude was between 225–500.

TABLE 2

| No *B. melitensis* Amplicons | | | | | | |
|---|---|---|---|---|---|---|
| | Bkgd | *B. abortus* | *B. melitensis* | *B. suis* | B. mix | Positive Control |
| | 234 | 3338 | 723 | 1635 | 624 | 74696 |
| | 720 | 1906 | 343 | 401 | 630 | 106775 |
| Avg. | 477 | 2622 | 533 | 1018 | 627 | 90736 |
| SD | 344 | 1013 | 269 | 873 | 4 | 22683 |
| CV | 72% | 39% | 50% | 86% | 1% | 25% |

TABLE 3

| Purified *B. melitensis* Amplicons | | | | | | |
|---|---|---|---|---|---|---|
| | Bkgd | *B. abortus* | *B. melitensis* | *B. suis* | B. mix | Positive Control |
| | 1179 | 5620 | 43185 | 2635 | 23020 | 65981 |
| | 693 | 5783 | 35862 | 2636 | 20792 | 68436 |
| | 754 | 4491 | 32250 | 2057 | 16263 | 81495 |
| | 394 | 5299 | 43165 | 2756 | 22929 | 46564 |
| Avg. | 755 | 5298 | 38616 | 2521 | 20751 | 65619 |
| SD | 323 | 575 | 5467 | 315 | 3164 | 14413 |
| CV | 43% | 11% | 14% | 12% | 15% | 22% |

As shown above, the *B. melitensis* target zone produces a much higher signal than the other *Brucella* species when the *B. melitensis* amplicon is used in the present invention.

Example 5

Concentration Dependent Detection of NosT Amplicon in Genetically Modified Plant Material Bio-discs were prepared as in Example 2, with NosT 52-mer oligonucleotide capture probes applied to the target zones. NosT is a marker gene for genetically modified plant material.

GMO reference materials, consisting of soya bean powder containing different mass fractions of powder from genetically modified soya beans, were obtained from Fluka BioChemika, certified reference material IRMM-410R (0, 0.1, 0.5, 1, 2, 5% Roundup Ready Soya). DNA was extracted from each of the six reference materials, using the WIZARD® Magnetic DNA Purification System for Food (Promega, Madison, Wis.).

The extracted DNA was subjected to PCR amplification using biotinylated forward/reverse primer sets directed to NosT to generate biotinylated 280-mer target NosT amplicons. Each reaction contained 50 ng extracted DNA, 0.2 μM biotinylated forward and reverse primers, 0.2 mM dNTPs, 0.05 U/μl Taq polymerase, 3.0 mM $MgCl_2$ and 1× PCR buffer.

The enzyme assay was performed as in Example 3, using the NosT amplicons as target probes. The results are shown in Table 4.

TABLE 4

| % GMO | Event Counts |
|---|---|
| 0 | 70 |
| 0.1 | 160 |
| 0.5 | 520 |
| 1 | 627 |

TABLE 4-continued

| % GMO | Event Counts |
|---|---|
| 2 | 651 |
| 5 | 925 |

As shown in Table 4, the detectable signal (event counts) increased as the percentage of GMO material increased. Between 0% and 1% GMO, there was a 90% correlation between the amount of GMO material and the resulting signal.

Concluding Summary

All patents, patent applications, and other publications mentioned in this specification are incorporated herein in their entireties by reference.

While this invention has been described in detail with reference to a certain preferred embodiments, it should be appreciated that the present invention is not limited to those precise embodiments. Rather, in view of the present disclosure that describes the current best mode for practicing the invention, many modifications and variations would present themselves to those of skill in the art without departing from the scope and spirit of this invention. For example, the optical bio-disc molecular diagnostic-enzyme based detection methods and systems, of the present invention, may be readily modified and implemented to test for proteins, cells, cell surface markers, or any antigen in an immunoassay format. In this immunoassay implementation of the present invention, the capture probe may be an antibody having specific affinity to an analyte. The analyte may be an antigen including proteins, glycoproteins, cells, cell surface markers, or any antigen. The enzyme would then be conjugated to a second (signal) antibody, having an affinity to a different epitope on the same antigen and no affinity for the capture probe, and the enzyme substrate reaction and signal detection carried out as described above. Alternatively, labeled or tagged signal antibodies may be used as the reporter instead of the precipitate or pellet formation of the enzyme-substrate system described above. Labels may include, for example, fluorescent molecules and microparticles. The scope of the invention is, therefore, indicated by the following claims rather than by the foregoing description. All changes, modifications, and variations coming within the meaning and range of equivalency of the claims are to be considered within their scope.

What is claimed is:

1. An optical bio-disc, comprising:

a substrate at least partially spin coated with an active layer that adheres to a pellet formed by an enzyme reaction; and at least one strand of DNA having an affinity for the active layer such that the DNA is immobilized on the active layer in a target zone.

2. The optical bio-disc according to claim 1 wherein the active layer comprises nitrocellulose.

3. The optical bio-disc according to claim 1 wherein the substrate includes encoded information associated therewith, the encoded information being readable by a disc drive assembly to control rotation of the bio-disc.

4. The optical bio-disc according to claim 1 further comprising a reflective layer disposed between the surface of the substrate and the active layer.

5. The optical bio-disc according to claim 1 further comprising an enzyme, wherein the enzyme, when exposed to an enzyme substrate, produces a signal detectable by an incident beam of electromagnetic radiation.

6. The optical bio-disc according to claim 1 further comprising a flow channel in fluid communication with the target zone and an input site in fluid communication with the flow channel.

7. A method of testing for the presence of a target-nucleic acid in a test sample, said method comprising the steps of:
providing a bio-disc, the bio-disc comprising a substrate at least partially spin coated with an active layer that adheres to a pellet formed by an enzyme reaction, and at least one strand of capture-DNA having an affinity for the active layer such that the capture-DNA is immobilized on the active layer in a target zone, wherein the capture-DNA and the target-nucleic acid having at least some complementary sequence;
depositing the test sample on the target zone;
allowing any target-nucleic acid present in the test sample to hybridize with the capture-DNA;
providing a plurality of enzyme molecules;
binding the enzyme molecules to the target-nucleic acid such that enzyme molecules bound to the target-nucleic are immobilized within the target zone;
washing the target zone to remove any unbound enzyme molecules;
depositing onto the target zone at least one enzyme substrate that reacts with the enzyme molecules to produce at least one detectable signal; and
detecting any signal in the target zone to thereby determine whether target-nucleic acid is present in the test sample.

8. The method of claim 7, further comprising the step of amplifying the test sample with at least one DNA primer set specific to the target-nucleic acid, to thereby amplify any target-nucleic acid present in the test sample.

9. The method of claim 8, wherein the DNA primer is labeled with an affinity agent.

10. The method of claim 9, wherein the affinity agent is biotin.

11. The method of claim 9, wherein the enzyme molecules are conjugated with a binding agent that interacts with the affinity agent.

12. The method of claim 11, wherein the binding agent is selected from the group consisting of streptavidin and neutravidin.

13. The method of claim 7, wherein the enzyme is horseradish peroxidase.

14. The method of claim 13, wherein the enzyme substrate is selected from the group consisting of 3,3',5,5'-tetramethylbenzidine (TMB), 4-chloronaphthol/3,3'-diaminobenzidine, tetrahydrochloride (CN/DAB), 4-chloro-1-napthol (4-CN), 3-amino-9-ethyl carbazol (AEC), and 3,3'-diaminobenzidine tetrahydrochioride (DAB).

15. The method of claim 7, wherein the detectable signal is a precipitate, which adheres to the active layer.

16. The method of claim 7, further comprising the steps of:
providing a signal DNA, wherein the signal DNA has a portion of sequence complementary to the target-nucleic acid but not to the capture-DNA;
binding the enzyme molecules to the signal DNA; and
hybridizing the signal DNA to the target-nucleic acid, such that the enzyme molecules are bound to the target-nucleic acids via the signal DNA.

17. A method of making an optical bio-disc, said method comprising the steps of:
providing a substrate;
forming a target zone on the substrate;
spin coated at least the target zone with an active layer that adheres to a pellet formed by an enzyme reaction;
encoding information on an information layer associated with the substrate, the encoded information being readable by a disc drive assembly to control rotation of the disc; and
depositing within the target zone, a plurality of strands of capture-DNA, at least some of the capture-DNA attaching to the active layer to thereby become immobilized within the target zone.

18. The method of claim 17, further comprising the step of forming a flow channel in fluid communication with said target zone.

19. The method of claim 18, further comprising the step of forming a chamber in fluid communication with the flow channel, the chamber having an input port.

20. The method of claim 19, further comprising the step of providing a pad on which an enzyme has been dried, wherein the pad is disposed with the chamber.

* * * * *

UNITED STATES PATENT AND TRADEMARK OFFICE
CERTIFICATE OF CORRECTION

PATENT NO. : 7,083,920 B2  
APPLICATION NO. : 10/150702  
DATED : August 1, 2006  
INVENTOR(S) : Werner et al.

It is certified that error appears in the above-identified patent and that said Letters Patent is hereby corrected as shown below:

In Column 30, Line 8 In Claim 14, delete "tetrahydrochioride" and insert -- tetrahydrochloride - --, therefor.

In Column 30, Line 24 In Claim 17, delete "coated" and insert -- coating --, therefor.

Signed and Sealed this

Thirteenth Day of February, 2007

JON W. DUDAS  
*Director of the United States Patent and Trademark Office*